US012697305B2

(12) United States Patent
Fang et al.

(10) Patent No.: US 12,697,305 B2
(45) Date of Patent: Aug. 4, 2026

(54) DELAYED RELEASE SOFTGEL CAPSULES

(71) Applicant: R.P. Scherer Technologies, LLC, Carson City, NV (US)

(72) Inventors: Qi Fang, St. Petersburg, FL (US); Karunakar Sukuru, St. Petersburg, FL (US)

(73) Assignee: R.P. Scherer Technologies, LLC, Carson City, NV (US)

( * ) Notice: Subject to any disclaimer, the term of this patent is extended or adjusted under 35 U.S.C. 154(b) by 722 days.

(21) Appl. No.: 17/928,955

(22) PCT Filed: Jun. 1, 2021

(86) PCT No.: PCT/US2021/035175
§ 371 (c)(1),
(2) Date: Dec. 1, 2022

(87) PCT Pub. No.: WO2021/247518
PCT Pub. Date: Dec. 9, 2021

(65) Prior Publication Data
US 2023/0225980 A1      Jul. 20, 2023

Related U.S. Application Data

(60) Provisional application No. 63/033,417, filed on Jun. 2, 2020.

(51) Int. Cl.
*A61K 9/48*          (2006.01)
*A61K 45/06*        (2006.01)

(52) U.S. Cl.
CPC .......... *A61K 9/4825* (2013.01); *A61K 9/4833* (2013.01); *A61K 9/4858* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,614,217 A * | 3/1997 | Chiprich | A61K 9/4825 424/451 |
| 2004/0224020 A1 | 11/2004 | Schoenhard | |
| 2005/0069579 A1 | 3/2005 | Kamaguchi et al. | |
| 2012/0301546 A1* | 11/2012 | Hassan | A23L 33/10 426/103 |
| 2015/0004226 A1 | 1/2015 | Baes et al. | |
| 2015/0366814 A1 | 12/2015 | Hu et al. | |
| 2016/0000740 A1 | 1/2016 | Zhang | |
| 2017/0119680 A1 | 5/2017 | Mcguffy | |
| 2017/0296474 A1* | 10/2017 | Masuda | A61K 9/4866 |
| 2018/0169051 A1* | 6/2018 | Zhang | A61K 31/202 |

FOREIGN PATENT DOCUMENTS

| | | |
|---|---|---|
| CA | 3055940 A1 | 9/2018 |
| CN | 104644609 A | 5/2015 |
| CO | 2020011165 | 11/2020 |
| CO | 2021012391 A2 | 10/2021 |
| CO | 2021018071 A2 | 4/2022 |
| CO | 2022001783 A2 | 4/2022 |
| CO | 2022005947 A2 | 7/2022 |
| CO | 2022007168 A2 | 8/2022 |
| CO | 2022014130 A2 | 10/2022 |
| CO | 42246 | 3/2024 |
| EP | 3205339 A1 | 8/2017 |
| EP | 4156971 A1 | 4/2023 |
| JP | H0427352 A | 1/1992 |
| JP | 2010047548 A | 3/2010 |
| JP | 2020516687 A | 6/2020 |
| KR | 20010016482 A | 3/2001 |
| RU | 2822392 C2 | 7/2024 |
| WO | 0217886 A1 | 3/2002 |
| WO | 03020049 A2 | 3/2003 |
| WO | 2010044736 A1 | 4/2010 |
| WO | 2015035513 A1 | 3/2015 |
| WO | 2015200149 A1 | 12/2015 |
| WO | 2019178444 A1 | 9/2019 |
| WO | 2020247352 A1 | 12/2020 |
| WO | 2021086848 A1 | 5/2021 |

OTHER PUBLICATIONS

Gelatin Shell Material and Formulations for Soft gels: An In-Depth Guide https://www.pharmaexcipients.com/news/material-formulations-softgels/#:~:text=Softgels%20typically%20use%20gelatin%20with,controlled%20to%20ensure%20proper%20encapsulation. (Year: 2024).*
International Search Report and Written Opinion for PCT/US2021/035175 mailed Oct. 14, 2021, 14 pages.
Cortesi, R., et al., "Sugar Cross-linked Gelatin for Controlled Release: Microspheres and Disks," Biomaterials, Sep. 1998, vol. 19(18), pp. 1641-1649.
Ming Y., et al., "Pharmaceutics, 2nd Edition," Chemical Medical Science and Technology Press, Aug. 31, 2018, pp. 143-145.
Office Action for Chinese Patent Application No. CN202180058038.2, mailed Oct. 29, 2025, 27 Pages.
Office Action for Korean Patent Application No. KR1020227045815, mailed Oct. 30, 2025, 30 Pages.

* cited by examiner

*Primary Examiner* — Robert A Wax
*Assistant Examiner* — Andre Mach
(74) *Attorney, Agent, or Firm* — Lowenstein Sandler LLP

(57)          ABSTRACT

Delayed release softgel capsules comprise a fill material and a pH dependent shell composition, characterized in that the delayed release nature of the capsules may be achieved without a pH dependent coating or added conventional pH dependent polymers. The delayed release softgel capsules described herein are particularly suitable for initiating release of the active agent in a target location in the colon environment.

18 Claims, 1 Drawing Sheet

Pectin Gel Aging Study

DELAYED RELEASE SOFTGEL CAPSULES

CROSS REFERENCE TO RELATED APPLICATION(S)

The present application is a national stage entry under 35 U.S.C. § 371 of International Application No. PCT/US2021/035175, filed on Jun. 1, 2021, which claims priority to United States Provisional Patent Application No. 63/033,417, filed on Jun. 2, 2020, which are herein incorporated by reference in their entirety.

FIELD OF THE INVENTION

The present invention relates to delayed release softgel capsules, wherein the gelatin-based shell compositions possess delayed release properties without the need for pH dependent coatings or the addition of conventional pH dependent synthetic polymers. Delayed release softgel capsules described herein are particularly suitable for colonic delivery.

BACKGROUND OF THE INVENTION

Soft capsules, in particular, soft gelatin capsules (or softgel capsules), provide a dosage form which is more readily accepted by patients, since the capsules are easy to swallow and need not be flavored in order to mask any unpleasant taste of the active agent. Softgel encapsulation of drugs further provides the potential to improve the bioavailability of the pharmaceutical agents. For example, active ingredients may be rapidly released in liquid form as soon as the gelatin shell ruptures.

Efforts have been made to create delayed release dosage forms. Delayed release dosage forms are designed to protect the contents of the dosage forms from gastric conditions. For example, delayed release dosage forms may be produced by adding a pH dependent coating to the surface of a manufactured dosage form such as a tablet or a capsule. Such coatings may be applied through spraying the dosage form, followed by drying the dosage form, usually at elevated temperatures. This method of coating a capsule with a pH dependent coating may lead to disadvantages in terms of performance and appearance. For example, the capsule may appear rough, the coating may be applied unevenly, and/or the coating can be prone to cracking or flaking off the dosage form. Additionally, the process of applying a pH dependent coating is very inefficient.

Other delayed release dosage forms have been developed in which conventional pH dependent polymers (i.e., acid-insoluble polymers) are added in the capsule shell. However, the addition of conventional pH dependent polymers can lead to capsules that are prone to leaking due to insufficient sealing.

Accordingly, there is currently a need for a delayed release softgel capsule that does not require either an application of a pH dependent coating or the addition of conventional pH dependent polymers in the shell.

SUMMARY OF THE INVENTION

The present invention is directed to delayed release softgel capsules. The delayed release softgel capsules comprise (a) a fill material and (2) a pH dependent shell composition. The delayed release softgel capsules according to the present invention do not require either a pH dependent coating or an added conventional pH dependent polymer. Accordingly, the pH dependent shell composition eliminates the need to add a pH dependent coating, which also minimizes the risk of damaging the capsules during the coating process. Delayed release softgel capsules described herein are particularly suitable for colonic delivery.

In an embodiment, the pH dependent shell composition comprises: (a) a gelatin, (b) dextrose, (c) a pectin such as a low methoxy pectin and optionally (d) a plasticizer. The pH dependent shell composition (e.g., amount of pectin, amount of dextrose, gelatin to pectin ratio) and its preparation process (e.g., curing duration, ribbon thickness) may be tuned/adjusted/modified to attain a target pH dissolution profile of the shell composition at various pH environments (e.g., rupture/dissolution/disintegration time in acidic medium and in buffer medium). The present invention is also directed to a process of making delayed release softgel capsules. In particular, the amount of dextrose in the pH dependent shell composition described herein may be adjusted to delay the release of the active agent until it reaches the colonic environment in a human subject.

The present invention is also directed to a method of treating a condition (e.g., colon disease or other condition that is treatable by targeted administration of an active agent to the colon) by administering to a subject any of the delayed release softgel compositions described herein. The delivery can be to treat a colon disease or condition and can also be used to treat a systemic condition with a drug that is suitable for absorption in the colon.

The present invention is also directed to a method of delivering an active agent to the colon of a patient by orally administering any of the delayed release softgel capsules described herein. In certain embodiments, at least 80%, at least 85%, at least 90%, at least 95%, or at least 99% of the active agent is delivered to the colon of the patient.

BRIEF DESCRIPTION OF THE DRAWINGS

The above and other features of the present disclosure, their nature, and various advantages will become more apparent upon consideration of the following detailed description, taken in conjunction with the accompanying drawings, in which:

FIG. 1 illustrates viscosity of shell compositions with amidated pectin and without amidated pectin as a function of aging time.

DETAILED DESCRIPTION OF THE INVENTION

The present invention advances the state of the art by developing delayed release oral dosage forms, in particular, delayed release softgel capsules, that achieve the advantages associated with the conventional delayed release dosage forms without the need to apply a pH dependent coating or to add conventional pH dependent synthetic polymer in the capsule shell. The delayed release softgel capsules of the present invention do not dissolve in a gastric environment of the stomach, but rather dissolve in the intestines, in particular in the colon of a human subject. The dissolution profile of the delayed release softgel capsules described herein can be tuned by modifying the shell composition of the softgel capsules.

Such mechanism is beneficial for delivery of active ingredients that may cause stomach irritation or are sensitive to the acidic environment of the stomach. Such mechanism is also beneficial for reducing belching after consuming capsules that encapsulate fill materials that tend to contribute to belching. For instance, belching often occurs upon consuming vitamin, minerals, supplements, and/or pharmaceutical products that are formulated in dosage form exhibiting some leaking (even of a very small amount), in the stomach, before reaching the intestines. The leakage can be particularly problematic when the belching is associated with substances that have a noisome perception such as fish oil and garlic that are commonly delivered in softgels. The delayed release softgel capsules described herein may be formulated in a manner that minimizes and/or eliminates premature leakage (and consequently premature release of the capsule's fill) in the gastric environment of the stomach and in any other area of the gastrointestinal tract preceding the colon.

As used herein, the term "pH dependent" is used to refer to the dissolution or disintegration resistant property of a substance such that dissolution or disintegration does not occur or does not substantially occur in a gastric environment of the stomach and in any other area of the gastrointestinal tract preceding the colon, e.g., for a time period of at least about 15 minutes, at least about 30 minutes, at least about one hour, at least about two hours, at least about three hours, at least about four hours, or at least about five hours. In certain embodiments, the gastric environment of the stomach may be simulated here with 0.1N HCl and optionally with the addition of pepsin. It should be noted that pharmacopeial methods do not include pepsin, however, pepsin was added in certain dissolution/disintegration tests described herein to better simulate/mimic in-vivo conditions. Hence, without being construed as limited, in certain embodiments, the compositions described herein are resistant to dissolution/disintegration for the durations outlined above even at 0.1N HCl environments that include Pepsin, an enzyme (which is presumed to be a more aggressive environment than 0.1N HCl without Pepsin).

For example, the embodiments described herein include a pH dependent shell composition that preferentially dissolves in pH of about 3.5 or higher (e.g., in biological, artificial or simulated colon environment and/or intestinal fluid) as compared to biological, artificial or simulated gastric fluid. For instance, the pH dependent shell composition dissolves in pH of about 3.5 or higher (e.g., in biological, artificial or simulated colon environment and/or intestinal fluid) after at least about 10 minutes, after at least about 15 minutes, after at least about 20 minutes, after at least about 25 minutes, after at least about 30 minutes, after at least about 35 minutes, after at least about 40 minutes, or from any of about 10 minutes, about 15 minutes, about 20 minutes, about 25 minutes or about 30 minutes up to any of about 35 minutes, about 40 minutes, about 45 minutes, about 50 minutes, about 55 minutes, about 60 minutes, about 75 minutes, or about 90 minutes, or any single value or sub-range therein. In certain embodiments, the colon or intestinal environment may be simulated here with pH 6.8 phosphate buffer and optionally with the addition of pancreatin. It should be noted that pharmacopeial methods do not include pancreatin, however, pancreatin was added in certain dissolution/disintegration tests described herein to better simulate/mimic in-vivo conditions. Hence, without being construed as limited, in certain embodiments, the compositions described herein exhibit similar dissolution/disintegration profiles at pH 6.8 buffer environments that include Pancreatin (which is presumed to be a more aggressive environment that pH 6.8 buffer environment without Pancreatin).

As used herein, "pharmaceutically active ingredient," "active agents" refers to a drug or compound that may be used in the diagnosis, cure, mitigation, treatment, or prevention of a condition. In certain embodiments, suitable "active agents" include nutraceuticals, such as, vitamins, minerals, and supplements (VMS). Exemplary delayed release softgel capsules may include, without limitations, capsules containing lactic acid bacteria, probiotics, fish oil capsules, valproic acid, garlic, peppermint oil, polyethylene glycol, ibuprofen solution or suspension, proton pump inhibitors, aspirin and similar products.

The term "condition" or "conditions" refers to those medical conditions that can be treated or prevented by administration to a subject of an effective amount of an active agent.

As used herein, the term "active ingredient" refers to any material that is intended to produce a therapeutic, prophylactic, or other intended effect, whether or not approved by a government agency for that purpose. This term with respect to a specific agent includes the pharmaceutically active agent, and all pharmaceutically acceptable salts, solvates and crystalline forms thereof, where the salts, solvates and crystalline forms are pharmaceutically active.

Any pharmaceutically active ingredient may be used for purposes of the present invention, including both those that are water-soluble and those that are poorly soluble in water. Suitable pharmaceutically active ingredients include, without limitation, analgesics and anti-inflammatory agents (e.g., ibuprofen, naproxen sodium, aspirin), antacids, anthelmintic, anti-arrhythmic agents, anti-bacterial agents, anticoagulants, anti-depressants, anti-diabetics, anti-diarrheal, anti-epileptics, anti-fungal agents, anti-gout agents, anti-hypertensive agents, anti-malarial, anti-migraine agents, anti-muscarinic agents, anti-neoplastic agents and immunosuppressants, anti-protozoal agents, anti-rheumatics, antithyroid agents, antivirals, anxiolytics, sedatives, hypnotics and neuroleptics, beta-blockers, cardiac inotropic agents, corticosteroids, cough suppressants, cytotoxics, decongestants, diuretics, enzymes, anti-parkinsonian agents, gastrointestinal agents, histamine receptor antagonists, lipid regulating agents, local anesthetics, neuromuscular agents, nitrates and anti-anginal agents, nutritional agents, opioid analgesics, anticonvulsant agents (e.g., valproic acid), oral vaccines, proteins, peptides and recombinant drugs, sex hormones and contraceptives, spermicides, stimulants, and combinations thereof.

In certain embodiments, the active agent which is contained in the capsule may be any pharmaceutically or therapeutically active agent which is desirable to deliver to the small intestine, for example pancreatin and other proteolytic enzymes, diclofenac, naproxen, aspirin, indomethacin, omeprazole, cardiac glycosides, electrolyte preparations with sodium, potassium and magnesium salts as well as calcium and iron preparations, bisacodyl preparations and valproic acid.

In certain embodiments, the active agent may be drugs which are desirable to deliver to the colon include drugs for the treatment of colon disease, for example 5-ASA; steroids such as hydrocortisone, budesonide; laxatives; octreotide; cisapride; anticholinergies; calcium channel blockers, 5HT3-antagonists such as ondansetron and peptides such as insulin.

In certain embodiments, active agents that are suitable for colonic delivery are, without limitations, one or more of, antiinfectives such as antibiotics and antiviral agents; analgesics and analgesic combinations; anorexics; helminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators; including general coronary, peripheral and cerebral; central nervous system stimulants; vasoconstrictors; cough and cold preparations including decongestants; hormones such as estradiol and other steroids, including corticosteroids; hypnotics; immunosuppressives; muscle relaxants; parasympatholytics; psychostimulants; sedatives; and tranquilizers; probiotics; anticancer agents (e.g., colon cancer specific anticancer agents or anticancer agents for other cancer types that can be treated systemically with an anticancer agent that is suitable for absorption in the colon).

Examples of colon cancer anticancer agents include, without limitations, Avastin (Bevacizumab), Bevacizumab, Camptosar (Irinotecan Hydrochloride), Capecitabine, Cetuximab, Cyramza (Ramucirumab), Eloxatin (Oxaliplatin), Erbitux (Cetuximab), 5-FU (Fluorouracil Injection), Fluorouracil Injection, Ipilimumab, Irinotecan Hydrochloride, Keytruda (Pembrolizumab), Leucovorin Calcium, Lonsurf (Trifluridine and Tipiracil Hydrochloride), Mvasi (Bevacizumab), Nivolumab, Opdivo (Nivolumab), Oxaliplatin, Panitumumab, Pembrolizumab, Ramucirumab, Regorafenib, Stivarga (Regorafenib), Trifluridine and Tipiracil Hydrochloride, Vectibix (Panitumumab), Xeloda (Capecitabine), Yervoy (Ipilimumab), Zaltrap (Ziv-Aflibercept), Ziv-Aflibercept, and any combinations thereof.

In some embodiments, the active pharmaceutical ingredient may be selected, without limitations, from the group consisting of dabigatran, dronedarone, ticagrelor, iloperidone, ivacaftor, midostaurine, asimadoline, beclomethasone, apremilast, sapacitabine, linsitinib, abiraterone, vitamin D analogs (e.g., calcifediol, calcitriol, paricalcitol, doxercalciferol), COX-2 inhibitors (e.g., celecoxib, valdecoxib, rofecoxib), tacrolimus, testosterone, lubiprostone, pharmaceutically acceptable salts thereof, and combinations thereof.

In some embodiments, the lipids in the dosage form may be selected, without limitations, from the group consisting of almond oil, argan oil, avocado oil, borage seed oil, canola oil, cashew oil, castor oil, hydrogenated castor oil, cocoa butter, coconut oil, colza oil, corn oil, cottonseed oil, grape seed oil, hazelnut oil, hemp oil, hydroxylated lecithin, lecithin, linseed oil, macadamia oil, mango butter, manila oil, mongongo nut oil, olive oil, palm kernel oil, palm oil, peanut oil, pecan oil, perilla oil, pine nut oil, pistachio oil, poppy seed oil, pumpkin seed oil, peppermint oil, rice bran oil, safflower oil, sesame oil, shea butter, soybean oil, sunflower oil, hydrogenated vegetable oil, walnut oil, and watermelon seed oil. Other oil and fats may include, but not be limited to, fish oil (omega-3), krill oil, animal or vegetable fats, e.g., in their hydrogenated form, free fatty acids and mono-, di-, and tri-glycerides with C8-, C10-, C12-, C14-, C16-, C18-, C20- and C22-fatty acids, fatty acid esters like EPA and DHA 3, and combinations thereof.

According to certain embodiments, active agents may include lipid-lowering agents including, but not limited to, statins (e.g., lovastatin, simvastatin, pravastatin, fluvastatin, atorvastatin, rosuvastatin, and pitavastatin), fibrates (e.g, clofibrate, ciprofibrate, bezafibrate, fenofibrate, and gemfibrozil), niacin, bile acid sequestrants, ezetimibe, lomitapide, phytosterols, and the pharmaceutically acceptable salts, hydrates, solvates and prodrugs thereof, mixtures of any of the foregoing, and the like.

Suitable nutraceutical active agents may include, but are not limited to, 5-hydroxytryptophan, acetyl L-carnitine, alpha lipoic acid, alpha-ketoglutarates, bee products, betaine hydrochloride, bovine cartilage, caffeine, cetyl myristoleate, charcoal, chitosan, choline, chondroitin sulfate, coenzyme Q10, collagen, colostrum, creatine, cyanocobalamin (Vitamin 812), dimethylaminoethanol, fumaric acid, germanium sesquioxide, glandular products, glucosamine HCl, glucosamine sulfate, hydroxyl methyl butyrate, immunoglobulin, lactic acid, L-Carnitine, liver products, malic acid, maltose-anhydrous, mannose (d-mannose), methyl sulfonyl methane, phytosterols, picolinic acid, pyruvate, red yeast extract, S-adenosylmethionine, selenium yeast, shark cartilage, theobromine, vanadyl sulfate, and yeast.

Suitable nutritional supplement active agents may include vitamins, minerals, fiber, fatty acids, amino acids, herbal supplements or a combination thereof.

Suitable vitamin active agents may include, but are not limited to, the following: ascorbic acid (Vitamin C), B vitamins, biotin, fat soluble vitamins, folic acid, hydroxycitric acid, inositol, mineral ascorbates, mixed tocopherols, niacin (Vitamin B3), orotic acid, para-aminobenzoic acid, panthothenates, panthothenic acid (Vitamin B5), pyridoxine hydrochloride (Vitamin B6), riboflavin (Vitamin B2), synthetic vitamins, thiamine (Vitamin B1), tocotrienols, vitamin A, vitamin D, vitamin E, vitamin F, vitamin K, vitamin oils and oil soluble vitamins.

Suitable herbal supplement active agents may include, but are not limited to, the following: arnica, bilberry, black cohosh, cat's claw, chamomile, echinacea, evening primrose oil, fenugreek, flaxseed, feverfew, garlic oil, ginger root, ginko biloba, ginseng, goldenrod, hawthorn, kava-kava, licorice, milk thistle, psyllium, rauowolfia, senna, soybean, St. John's wort, saw palmetto, turmeric, valerian.

Minerals active agents may include, but are not limited to, the following: boron, calcium, chelated minerals, chloride, chromium, coated minerals, cobalt, copper, dolomite, iodine, iron, magnesium, manganese, mineral premixes, mineral products, molybdenum, phosphorus, potassium, selenium, sodium, vanadium, malic acid, pyruvate, zinc and other minerals.

Examples of other possible active agents include, but are not limited to, antihistamines (e.g., ranitidine, dimenhydrinate, diphenhydramine, chlorpheniramine and dexchlorpheniramine maleate), non-steroidal anti-inflammatory agents (e.g., aspirin, celecoxib, Cox-2 inhibitors, diclofenac, benoxaprofen, flurbiprofen, fenoprofen, flubufen, indoprofen, piroprofen, carprofen, oxaprozin, pramoprofen, muroprofen, trioxaprofen, suprofen, aminoprofen, fluprofen, bucloxic acid, indomethacin, sulindac, zomepirac, tiopinac, zidometacin, acemetacin, fentiazac, clidanac, oxpinac, meclofenamic acid, flufenamic acid, niflumic acid, tolfenamic acid, diflurisal, flufenisal, piroxicam, sudoxicam, isoxicam, aceclofenac, aloxiprin, azapropazone, benorilate, bromfenac, carprofen, choline magnesium salicylate, diflunisal, etodolac, etoricoxib, faislamine, fenbufen, fenoprofen, flurbiprofen, ibuprofen, indometacin, ketoprofen, ketorolac, lornoxicam, loxoprofen, meloxicam, mefenamic acid, metamizole, methyl salicylate, magnesium salicylate, nabumetone, naproxen, nimesulide, oxyphenbutazone, parecoxib, phenylbutazone, salicyl salicylate, sulindac, sulfinpyrazone, tenoxicam, tiaprofenic acid, tolmetin. pharmaceutically acceptable salts thereof and mixtures thereof) and acetaminophen, anti-emetics (e.g., metoclopramide, methylnaltrexone), anti-epileptics (e.g., phenyloin, meprobmate and nitrazepam), vasodilators (e.g., nifedipine, papaverine, diltiazem and nicardipine), anti-tussive agents and expectorants (e.g. codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluthiazide), anti-hypotensives (e.g., propranolol, clonidine), antihypertensives (e.g., clonidine, methyldopa), bronchodilatiors (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants (e.g. pseudoephedrine), laxatives, vitamins, stimulants (including appetite suppressants such as phenylpropanolamine) and cannabinoids, as well as pharmaceutically acceptable salts, hydrates, solvates, and prodrugs thereof.

The active agent that may also be a benzodiazepine, barbiturate, stimulants, or mixtures thereof. The term "benzodiazepines" refers to a benzodiazepine and drugs that are derivatives of a benzodiazepine that are able to depress the central nervous system. Benzodiazepines include, but are not limited to, alprazolam, bromazepam, chlordiazepoxide, clorazepate, diazepam, estazolam, flurazepam, halazepam, ketazolam, lorazepam, nitrazepam, oxazepam, prazepam, quazepam, temazepam, triazolam, as well as pharmaceutically acceptable salts, hydrates, solvates, prodrugs and mixtures thereof. Benzodiazepine antagonists that can be used as active agent include, but are not limited to, flumazenil as well as pharmaceutically acceptable salts, hydrates, solvates and mixtures thereof.

The term "barbiturates" refers to sedative-hypnotic drugs derived from barbituric acid (2,4,6,-trioxohexahydropyrimidine). Barbiturates include, but are not limited to, amobarbital, aprobarbotal, butabarbital, butalbital, methohexital, mephobarbital, metharbital, pentobarbital, phenobarbital, secobarbital as well as pharmaceutically acceptable salts, hydrates, solvates, prodrugs, and mixtures thereof. Barbiturate antagonists that can be used as active agent include, but are not limited to, amphetamines as well as pharmaceutically acceptable salts, hydrates, solvates and mixtures thereof.

The term "stimulants" includes, but is not limited to, amphetamines such as dextroamphetamine resin complex, dextroamphetamine, methamphetamine, methylphenidate, as well as pharmaceutically acceptable salts, hydrates, and solvates and mixtures thereof. Stimulant antagonists that can be used as active agent include, but are not limited to, benzodiazepines, as well as pharmaceutically acceptable salts, hydrates, solvates and mixtures thereof.

The dosage forms according to the disclosure include various active agents and their pharmaceutically acceptable salts thereof. Pharmaceutically acceptable salts include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like, and metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like.

As used herein, the terms "therapeutically effective" and an "effective amount" refer to the amount of active agent or the rate at which it is administered which is needed to produce a desired therapeutic result.

As used herein, "shell" or "shell composition" or "pH dependent shell composition" refers to the shell of a softgel capsule which encapsulates a fill material.

As used herein, "conventional pH dependent polymers" refer to, but are not limited to, acrylic and methacrylic acid polymers, which may be available under the tradename EUDRAGIT® and other conventional acid insoluble polymers, e.g., methyl acrylate-methacrylic acid copolymers. Other conventional acid insoluble polymers include, without limitation, cellulose acetate succinate, cellulose acetate phthalate, cellulose acetate butyrate, hydroxypropyl methyl cellulose phthalate, hydroxy propyl methyl cellulose acetate succinate (hypermellose acetate succinate), polyvinyl acetate phthalate (PVAP), algenic acid salts such as sodium alginate and potassium alginate, stearic acid, and shellac. Pectin and pectin derivatives are not considered to be conventional pH dependent polymers. In some embodiments, the pH dependent shell composition of the present invention does not include an acid insoluble polymer. In other words, in certain embodiments, the pH dependent shell composition and the pH dependent softgel capsule are "free or substantially free of conventional pH dependent polymers."

As used herein, "free or substantially free," refers to a composition that comprises less than about 1 wt %, less than about 0.5 wt %, less than about 0.25 wt %, less than about 0.1 wt %, less than about 0.05 wt %, less than about 0.01 wt %, or 0 wt % of said component.

All references to wt % throughout the specifications and the claims refer to the weight of the component in reference to the weight of the entire subject composition and may also be designated as w/w.

As used herein, "fill material" or "fill" refers to the composition that is encapsulated by the pH dependent shell composition and contains at least one pharmaceutically active ingredient.

As used herein, "delayed release capsules" or "delayed release softgel capsules" or "pH dependent capsules" or "pH dependent softgel capsules" refer to capsules which have delayed or pH dependent properties once the fill material is encapsulated in the shell, and the capsules are dried. In certain embodiments, these terms may refer to capsules that have also been cured after drying. In certain embodiments, no further processing steps after drying are required. In certain embodiments, no further processing steps after curing are required.

As used herein, "about" refers to any values that are within a variation of ±10%, such that "about 10" would include from 9 to 11. As used herein, "a," "an," or "the" refers to one or more, unless otherwise specified. Thus, for example, reference to "an excipient" includes a single excipient as well as a mixture of two or more different excipients, and the like.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

According to a first embodiment, a pH dependent softgel capsule comprises (a) a fill material and (b) a pH dependent shell composition, wherein the fill material comprises at least one pharmaceutically active ingredient, wherein the pH dependent shell composition comprises a gelatin, dextrose, a pH dependent material (e.g., a low methoxyl pectin) and optionally a plasticizer. Preferably, the pH dependent shell composition is free of additional pH dependent polymers. In certain embodiments, the pH dependent softgel capsule or the pH dependent shell composition is configured to remain intact in acidic medium, such as the stomach environment or a simulated gastric fluid environment (e.g., for a duration of at least about 5 hours, at least about 4 hours, at least about 3 hours, at least about 2 hours, at least about 1 hour, and the like), and to dissolve/disintegrate in the colon (or a simulated intestinal fluid environment) in a target duration (e.g., after at least about 10 minutes, after at least about 15 minutes, after at least about 20 minutes, after at least about 25 minutes, after at least about 30 minutes, after at least about 35 minutes, after at least about 40 minutes, or from any of above 0 minutes, about 5 minutes, about 10 minutes, about 15 minutes, about 20 minutes, about 25 minutes or about 30 minutes up to any of about 35 minutes, about 40 minutes, about 45 minutes, about 50 minutes, about 55 minutes, about 60 minutes, about 75 minutes, or about 90 minutes, or any single value or sub-range therein).

Suitable fill materials comprise at least one pharmaceutically active ingredient and can be made according to known methods. In addition to the at least one pharmaceutically active ingredient, suitable fill materials may comprise additional fill components such as flavoring agents, sweetening agents, coloring agents and fillers or other pharmaceutically acceptable excipients or additives such as synthetic dyes and mineral oxides. Suitable amounts of pharmaceutically active ingredient and pharmaceutically acceptable excipients can be readily determined by one of ordinary skill in the art.

In an embodiment, the gelatin in the pH dependent shell composition may include Type A gelatin, Type B gelatin, a hide or skin gelatin (e.g., calf skin, pig skin) and/or a bone gelatin (e.g., calf bone, pig bone) used alone or in combination. In one embodiment, the gelatin is a 250 Bloom gelatin. In another embodiment, there is only one type of gelatin. In yet another embodiment, the gelatin is a combination of at least two types of gelatins. In an embodiment, the amount of gelatin in the pH dependent shell composition is from about 30 wt % to about 85 wt %, from about 30 wt % to about 75 wt %, from about 30 wt % to about 65 wt %, from about 30 wt % to about 55 wt %, from about 30 wt % to about 40 wt %, from about 40 wt % to about 80 wt %, from about 45 wt % to about 65 wt %, from about 45 wt % to about 75 wt %, or from about 50 wt % to about 70 wt %, or any single value or sub-range therein, based on total weight of the dry capsule shell composition.

In one embodiment, the pH dependent capsule shell composition comprises dextrose. In an embodiment, the amount of dextrose in the pH dependent capsule shell composition is from about 0.001 wt % to about 1.0 wt %, from about 0.002 wt % to about 0.008 wt %, from about 0.005 wt % or about 0.01 wt % to about 4 wt %, from about 0.1 wt % or about 0.15 wt % to about 3 wt %, from about 0.1 wt % to about 1 wt %, from about 0.1 or about 0.15 wt % to about 0.2 wt % or about 0.25 wt % to about 2 wt %, from about 0.1 wt % to about 0.2 wt %, from about 0.05 wt % or about 0.1 wt % to about 0.4 wt % or about 0.5 wt %, or any single value or sub-range therein, based on total weight of the dry capsule shell composition.

The dextrose may be added to the delayed release capsule shell to mitigate potential reduction in gel strength. The amount of dextrose in the pH dependent shell composition may also be tuned to attain a target dissolution profile for the delayed release softgel capsule, for instance, to have the delayed release softgel capsule dissolve/disintegrate in a particular location in the gastrointestinal tract (e.g., in the colon). In one embodiment, the amount of dextrose in the pH dependent shell composition is tuned to delay dissolution of the delayed release softgel capsule until it reaches the colon and to attain a target dissolution profile in the colon. For example, the amount of dextrose in the pH dependent shell composition may be tuned to prevent premature leakage/rupture in acidic medium (e.g., 0.1N HCl optionally with Pepsin) while controlling the time to dissolution/disintegration/rupture in buffer medium (e.g., pH 6.8 phosphate buffer optionally with Pancreatin to simulate the colon environment in a human subject). The time to dissolution/disintegration/rupture in the buffer stage may be controlled to be after at least about 10 minutes, after at least about 15 minutes, after at least about 20 minutes, after at least about 25 minutes, after at least about 30 minutes, after at least about 35 minutes, after at least about 40 minutes, or from any of about 10 minutes, about 15 minutes, about 20 minutes, about 25 minutes or about 30 minutes to any of about 35 minutes, about 40 minutes, about 45 minutes, about 50 minutes, about 55 minutes, about 60 minutes, about 75 minutes, or about 90 minutes, or any single value or sub-range therein. The dissolution/disintegration/rupture time in acidic medium may be controlled to maintain an intact delayed release softgel capsule for at least about 15 minutes, at least about 30 minutes, at least about 45 minutes, at least about 60 minutes, at least about 90 minutes, at least about 120 minutes, or at least about 150 minutes.

Without being construed as limiting, it is believed that the dextrose interacts with the gelatin in the shell composition and cause the gelatin to cross-link. The effect of the amount of dextrose on the dissolution properties of the shell composition is further illustrated in the examples. The concentration of dextrose in the pH dependent shell composition may be in an effective amount to improve the gel strength but not so high that it would interfere with the seal of the capsule or manufacturability of the product performance.

In some embodiments, the pH dependent shell composition may comprise pectin, e.g., a low methoxyl pectin. In an embodiment, the pectin is low methylester (LM) pectin with Degree of Esterification lower than 50. In some embodiments, the pectin is amidated pectin. In other embodiments, the low methoxyl (LM) pectin is non-amidated pectin. In certain embodiments, the pectin is a combination of amidated pectin and non-amidated pectin. The addition of pectin contributes to the pH dependent nature of the dosage form.

Too much pectin in the dosage form may reduce the gel strength of the softgel capsule which may in turn adversely affect the sealability of the softgel capsule. Too much pectin in the pH dependent shell composition may also increase the viscosity of the shell composition, making it challenging or impossible to process from a manufacturing standpoint.

Therefore, pectin may be added to the dosage form at a concentration that is sufficiently high to form a delayed release dosage form and at the same time is sufficiently low to mitigate the reduction in gel strength and to mitigate viscosity increase.

In an embodiment, an amount of pectin in the pH dependent shell composition is about 2 wt % to about 20 wt %, from about 3 wt % to about 15 wt %, from about 3 wt % to about 5.5 wt %, from about 4 wt % to about 11 wt %, from about 7 wt % to about 12 wt %, from about 8 wt % to about 13 wt %, or from about 5 wt % to about 10 wt %, or any single value or sub-range therein, based on total weight of the dry capsule shell composition.

The degree of esterification of the pectin incorporated in the pH dependent shell composition may be lower than about 50%, or may range from about 10% to about 50%, from about 20% to about 40%, or from about 25% to about 35%. Also, the pectin may be amidated or non-amidated.

In certain embodiments, the pH dependent shell composition comprises a stabilizer and/or a binder comprising gellan gum. In certain embodiments, the ratio of pectin to stabilizer and/or binder (e.g., gellan gum) is about 1:10 to about 50:1; about 1:5 to about 40:1; about 1:1 to about 25:1 or about 10:1 to about 24:1.

In certain embodiments, the amount of stabilizer and/or binder (e.g., gellan gum) in the pH dependent shell composition is about 0.05 wt % to about 5 wt %, about 0.1 wt % to about 3 wt %, or about 0.2 wt % to about 2 wt % of stabilizer and/or binder (e.g., gellan gum), or any single value or sub-range therein, based on total weight of the dry capsule shell composition.

In certain embodiments, the pH dependent shell composition may have a viscosity ranging from any of about 20,000 cPs, about 30,000 cPs, about 40,000 cPs, about 50,000 cPs, about 60,000 cPs, or about 70,000 cPs to any of about 80,000 cPs, about 90,000 cPs, about 100,000 cPs, about 110,000 cPs, about 120,000 cPs, about 130,000 cPs, about 140,000 cPs, or about 150,000 cPs, or any sub-range or single value therein. In one embodiment, the pH dependent shell composition has a viscosity ranging from about 100,000 cPs to about 130,000 cPs, or from about 110,000 cPs to about 125,000 cPs, or about 115,000 cPs, or about 120,000 cPs. The viscosity is measured using a rheometer at 60° C. as described in further detail in the examples related to FIG. 1. A gel mass sample (e.g., of any of the pH dependent shell compositions described herein) is loaded onto the platform of the rheometer, maintained at 60° C. A disc rotates at a certain speed to provide a fixed shear rate. The viscosity is obtained by measuring the shear stress and shear rate.

In certain embodiments, the pH dependent shell composition may maintain a viscosity that is suitable for manufacturability even after being aged in heat for up to about 24 hours, up to about 48 hours, up to about 72 hours, up to about 96 hours, or up to about 1 week. In certain embodiments, the viscosity of the pH dependent shell composition, after aging in heat (for up to about 24 hours, up to about 48 hours, up to about 72 hours, up to about 96 hours, or up to about 1 week) may reduce (from the viscosity value of the composition prior to aging) by up to about 80%, up to about 70%, up to about 60%, up to about 50%, up to about 40%, up to about 35%, or up to about 30%.

In an embodiment, the plasticizer in the pH dependent shell composition may include glycerol, glycerin, sorbitol and combinations thereof. Other suitable plasticizers may include, but not be limited to, sugar alcohol plasticizer such as isomalt, maltitol, xylitol, erythritol, adonitol, dulcitol, pentaerythritol, or mannitol; or polyol plasticizer such as diglycerin, dipropylene glycol, a polyethylene glycol up to 10,000 MW, neopentyl glycol, propylene glycol, 1,3-propanediol, 2-methyl-1,3-propanediol, trimethylolpropane, a polyether polyol, ethanol amines; and mixtures thereof. Other exemplary plasticizers may also include, without limitations, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, citrate ester-type plasticizers, and triacetin. Such plasticizers may include 1,2-butylene glycol, 2,3-butylene glycol, styrene glycol, mono-propylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, glyceryl monostearate, polysorbate 80, acetyl triethyl citrate, tributyl citrate and allyl glycolate, and mixtures thereof.

In an embodiment, the amount of plasticizer in the pH dependent shell composition is from about 15 wt % to about 45 wt %, from about 15 wt % to about 40 wt %, from about 18 wt % to about 45 wt %, from about 18 wt % to about 42 wt %, from about 20 wt % to about 35 wt %, from about 25 wt % to about 30 wt %, or any single value, or sub-range therein, based on total weight of the dry capsule shell composition.

In certain embodiments, the amount of the various components (e.g., pectin, dextrose, gelatin, plasticizer) and the ratio of the various components are tuned to control the dissolution and/or disintegration properties of the softgel capsule across various pH ranges.

For instance, the gelatin to pectin w:w ratio in the pH dependent shell composition may range from any of about 2:1, about 3:1, about 4:1, about 5:1, about 6:1, about 7:1, about 8:1, or about 9:1 to any of about 10:1, about 11:1, about 12:1, about 13:1, about 14:1, about 15:1, about 16:1, about 17:1, about 18:1, about 19:1, or about 20:1, or any sub-range or single value therein. In certain embodiments, lower gelatin to pectin w:w ratios provide for a pH dependent shell composition that is more stable (dissolves slower if at all) in acidic medium (e.g., 0.1N HCl optionally with Pepsin), while higher gelatin to pectin w:w ratios provide for a pH dependent shell composition that is less stable (dissolves faster) in acidic medium (e.g., 0.1N HCl optionally with Pepsin). The gelatin to pectin w:w ratio may be tuned to attain a particular dissolution time for softgel capsule in acidic medium (e.g., about 10 minutes, about 15 minutes, about 30 minutes, about 45 minutes, about 60 minutes, about 90 minutes, or any sub-range within these durations, and so on).

The gelatin to plasticizer w:w ratio in the pH dependent shell composition may also be tuned to attain a particular capsule hardness level and may range from about 5:1 to about 1:5, from about 4:1 to about 1:4, from about 3:1 to about 1:3, from about 2:1 to about 1:2, about 1:1, or any single ratio value or sub-range therein.

In certain embodiments, the pH dependent shell compositions described herein may have a hardness ranging from any of about 5 N, about 6 N, about 7 N, about 8 N, about 9 N, or about 10 N to any of about 11 N, about 12 N, about 13 N, about 14 N, or about 15 N. The capsule hardness is determined using a hardness tester. The force required to cause a 2.0 mm deformation of the capsule in Newton is defined as the capsule hardness.

In certain embodiments, the pH dependent shell compositions described herein may have a shell moisture ranging from any of about 5%, about 6%, about 7%, about 8%, about 9%, or about 10% to any of about 11%, about 12%, about 13%, about 14%, or about 15%. The shell moisture is determined by loss on drying method. A pH dependent capsule shell composition sample of 1 to 2 grams is placed into a 105° C. oven for 17 hours. The initial weight of the sample is recorded. After drying the sample in the oven at 105° C. for 17 hours, the final weight of the sample is recorded. The percentage of weight loss, calculated in accordance with the below equation, is defined as the shell moisture:

$$\% \text{ Weight Lost} = \frac{(\text{Initial Weight}) - (\text{Final Weight})}{(\text{Initial Weight})} \cdot 100\%$$

In certain embodiments, the pH dependent shell compositions described herein may have an equilibrium relative humidity ranging from any of about 25%, about 28%, about 30%, about 32%, about 34%, or about 35% to any of about 38%, about 40%, about 42%, about 45%, or about 50%. Equilibrium Relative Humidity (%) is defined as the humidity condition at which the capsule maintained a constant total weight. It is determined using environmental chambers maintained at constant humidity using saturated salt solutions.

In certain embodiments, the pH dependent shell compositions described herein may have a burst strength ranging from any of about 50 kg, about 60 kg, about 70 kg, about 80 kg, or about 90 kg to any of about 100 kg, about 110 kg, about 120 kg, about 130 kg, about 140 kg, or about 150 kg. Burst strength is determined using a texture analyzer. The texture analyzer compressed the capsule until the capsule burst. The force, in kilograms, required to make the capsule burst is defined as burst strength.

In an embodiment, the pH dependent shell composition and the pH dependent softgel capsule may be free or substantially free of conventional pH dependent polymers and/or be free of a pH dependent overcoat over the softgel shell.

In an embodiment, the pH dependent shell composition and the pH dependent softgel capsule may include divalent cation salts, such as $Ca^{++}$ (e.g., $CaCl_2$) or $Mg^{++}$ (e.g., $MgCl_2$). In another embodiment, the pH dependent shell composition and the pH dependent softgel capsule may be free or substantially free of divalent cation salts, such as $Ca^{++}$ (e.g., $CaCl_2$) or $Mg^{++}$ (e.g., $MgCl_2$). In a further embodiment, the pH dependent shell composition may not include the step of the addition of divalent cation salts, such as $Ca^{++}$ (e.g., $CaCl_2$) or $Mg^{++}$ (e.g., $MgCl_2$) other than an amount of divalent cation salts that me be present in other components.

In an embodiment, the pH dependent shell composition may optionally comprise additional agents such as stabilizers or binders (e.g., gellan gum), coloring agents, flavorings agents, sweetening agents, fillers, antioxidants, diluents, pH modifiers or other pharmaceutically acceptable excipients or additives such as synthetic dyes and mineral oxides.

Exemplary suitable coloring agents may include, but not be limited to, colors such as e.g., white, black, yellow, blue, green, pink, red, orange, violet, indigo, and brown. In specific embodiments, the color of the dosage form can indicate the contents (e.g., one or more active ingredients) contained therein.

Exemplary suitable flavoring agents may include, but not be limited to, "flavor extract" obtained by extracting a part of a raw material, e.g., animal or plant material, often by using a solvent such as ethanol or water; natural essences obtained by extracting essential oils from the blossoms, fruit, roots, etc., or from the whole plants.

Additional exemplary flavoring agents that may be in the dosage form may include, but not be limited to, breath freshening compounds like menthol, spearmint, and cinnamon, coffee beans, other flavors or fragrances such as fruit flavors (e.g., cherry, orange, grape, etc.), especially those used for oral hygiene, as well as actives used in dental and oral cleansing such as quaternary ammonium bases. The effect of flavors may be enhanced using flavor enhancers like tartaric acid, citric acid, vanillin, or the like.

Exemplary sweetening agents may include, but not be limited to, one or more artificial sweeteners, one or more natural sweeteners, or a combination thereof. Artificial sweeteners include, e.g., acesulfame and its various salts such as the potassium salt (available as Sunett®), alitame, aspartame (available as NutraSweet® and Equal®), salt of aspartame-acesulfame (available as Twinsweet®), neohesperidin dihydrochalcone, naringin dihydrochalcone, dihydrochalcone compounds, neotame, sodium cyclamate, saccharin and its various salts such as the sodium salt (available as Sweet'N Low®), stevia, chloro derivatives of sucrose such as sucralose (available as Kaltame® and Splenda®), and mogrosides. Natural sweeteners include, e.g., glucose, dextrose, invert sugar, fructose, sucrose, glycyrrhizin; monoammonium glycyrrhizinate (sold under the trade name MagnaSweet®); *Stevia rebaudiana* (Stevioside), natural intensive sweeteners, such as Lo Han Kuo, polyols such as sorbitol, mannitol, xylitol, erythritol, and the like.

In some embodiments, the pH dependent shell composition and/or the pH dependent softgel capsule may be tested in a disintegration/dissolution test performed in a USP Apparatus II with paddles at a speed of 50 rpm in acidic medium (e.g., pH 1.2 (0.1N HCl) optionally with Pepsin) followed by buffer medium for simulating the colon environment and/or intestinal fluid (e.g., pH 6.8 phosphate buffer optionally with Pancreatin, such as about 1% Pancreatin). The pH dependent softgel capsule according to this embodiment may remain intact for at least about 10 minutes, at least about 15 minutes, at least about 30 minutes, at least about one hour, at least about two hours, at least about three hours, at least about four hours, or at least about five hours, in acidic medium and may disintegrate in intestinal fluid and/or colon environment and/or in simulated intestinal fluid (such as, buffer medium) in after at least about 10 minutes, after at least about 15 minutes, after at least about 20 minutes, after at least about 25 minutes, after at least about 30 minutes, after at least about 35 minutes, after at least about 40 minutes, or from any of about 10 minutes, about 15 minutes, about 20 minutes, about 25 minutes or about 30 minutes to any of about 35 minutes, about 40 minutes, about 45 minutes, about 50 minutes, about 55 minutes, about 60 minutes, about 75 minutes, or about 90 minutes, or any single value or sub-range therein.

While the buffer medium of the two phase dissolution/disintegration test has a pH 6.8, it should be noted that a similar dissolution/disintegration profile may be attained at a buffer medium having a pH of about 3.5 or higher (optionally with Pancreatin). It should also be noted that the presence of Pepsin (in acidic medium) and Pancreatin (in buffer medium) or not necessitated by pharmacopeial methods but are used herein in certain instances to simulate more aggressive environments that better mimic in-vivo conditions.

In some embodiments, the two phase disintegration/dissolution test may be performed for a total (inclusive of both acidic medium and buffer medium) of about 420 minutes, about 360 minutes, about 300 minutes, about 240 minutes, about 210 minutes, about 180 minutes, about 150 minutes, about 120 minutes, about 105 minutes, about 90 minutes, about 75 minutes, about 60 minutes, about 45 minutes, about 30 minutes, about 15 minutes, about 10 minutes, or about 5 minutes.

Encapsulation of the fill material can be accomplished in any conventional manner. As an example, a rotary die encapsulation may be used.

According to an embodiment, a pH dependent softgel capsule is prepared by the process comprising the steps of: (a) preparing the fill material, said fill material comprising at least one pharmaceutically active ingredient; and (b) encapsulating the fill material of step (a) in a pH dependent shell composition. The encapsulation process according to step (b) may further comprise a sub-step of preparing the pH dependent shell composition by, for example, admixing a gelatin, dextrose, a pectin and optionally a plasticizer. Preferably, wherein the pH dependent shell composition is free of additional pH dependent polymers (such as conventional pH dependent synthetic polymers).

The ribbon thickness of the pH dependent shell composition (as used for example during rotary die encapsulation) may also be tuned to control the pH dependent dissolution profile of the final pH dependent softgel capsule. The ribbon thickness of the pH dependent shell composition may range, without limitations, from any of about 0.02 inches, about 0.022 inches, about 0.024 inches, about 0.026 inches, about 0.028 inches, or about 0.030 inches to any of about 0.032 inches, about 0.034 inches, about 0.036 inches, about 0.038 inches, about 0.04 inches, about 0.042 inches, about 0.044 inches, or about 0.050 inches or any sub-range or single value therein.

In certain embodiments, the pH dependent softgel capsule (e.g., after encapsulation) may be dried and optionally cured. Curing the softgel capsule may be performed at a temperature ranging from about 25° C. to about 75° C., about 25° C. to about 70° C., or from about 30° C. to about 60° C., or from about 35° C. to 50° C. The curing temperature should be high enough to enhance the delayed release properties of the softgel capsules but not so high that it would melt the softgel capsule.

The duration of curing may range from about 12 hours to about 168 hours, from about 18 hours to about 120 hours, from about 24 hours to about 72 hours, about 24 hours, about 48 hours, about 72 hours, or any sub-range or single values therein. In an embodiment, the curing of the softgel capsule may be performed at a temperature of about 40° C. for about 24 hours. In an embodiment, the curing of the softgel capsule may be performed at a temperature of about 40° C. for about 48 hours. In an embodiment, the curing of the softgel capsule may be performed at a temperature of about 40° C. for about 72 hours. In certain embodiments, the curing may occur in air (without any particular controls as to the content of nitrogen or oxygen or humidity). In certain embodiments, the curing may occur under inert conditions (e.g., in nitrogen).

In an embodiment, the process for preparing a pH dependent softgel capsule comprises, consists essentially of, or consists of a) preparing any of the fill materials described herein; b) encapsulating the fill material from step a) in any of the pH dependent shell compositions described herein (e.g., via rotary die encapsulation); c) drying the encapsulated pH dependent softgel capsules (e.g., by tumble drying or regular drying in a basket without tumbling); and optionally d) curing the pH dependent softgel capsule in accordance with any of the curing conditions described herein.

In certain embodiments, drying is performed at about 10° C. to about 50° C., about 15° C. to about 40° C., or about 20°

C. to about 35° C. at a relative humidity of about 5% to about 40%, about 10% to about 30%, or about 15% to about 25%.

In certain embodiments, reference to drying and curing should be distinguished here. The purpose of drying the delayed release softgel capsules described herein is to remove excess water from the delayed release softgel capsule immediately after encapsulation. So, the capsules will be physically stable. The purpose of curing the delayed release softgel capsules described herein is to enhance the delayed release property of the delayed release softgel capsule. Hence, the presence of a drying step is not the same as a curing step and similarly the presence of a curing step is not the same as a drying step.

In certain embodiments, delayed release softgel capsules having the pH dependent shell compositions described herein are chemically and physically stable.

For instance, their chemical stability may be evidenced by the content of the active agent in the fill material (e.g., content of fish oil constituents when the fill material includes fish oil). In certain embodiments, the content of the fill material constituents is substantially similar (or within specifications), after storage for up to 12 months, up to 6 months, up to 3 months, or up to 1 months (at ambient conditions or at stressed conditions of 40° C. and 75% relative humidity for any of these durations) as compared to the raw material before storage.

In certain embodiments, the physical stability of the delayed release softgel capsules may be evidenced by the dissolution profile of the capsule in acidic medium and in buffer medium. For instance, the dissolution profile of the capsule in acidic medium and in buffer medium is substantially similar (or within specifications), after storage for up to 12 months, up to 6 months, up to 3 months, or up to 1 months (at ambient conditions or at stressed conditions of 40° C. and 75% relative humidity for any of these durations) as compared to the dissolution profile of the capsule before storage.

The term "substantially similar" may refer to a particular value being within about 30%, within about 25%, within about 20%, within about 15%, within about 10%, within about 5%, or within about 1% of a corresponding comparative value. The percentage being calculated based on the face value of the comparative value. For instance, a dissolution time range of 27 minutes to 33 minutes may be considered within 10% of comparative dissolution time of 30 minutes.

In certain embodiments, the instant disclosure may also be directed to a method of stabilizing any of the delayed release softgel capsules described herein. The method may include protecting (e.g., from oxidation or another potential source of chemical degradation) any of the fill materials described herein by encapsulating any of the fill materials described herein (including at least one active agent) in any of the pH dependent shell compositions described herein.

In certain embodiments, the pH dependent shell composition described herein produce a robust delayed release softgel capsule that has little or no premature release of the fill material in acidic environment (e.g., stomach environment or simulated stomach environment such as simulated gastric fluid, 0.1N HCl optionally with Pepsin) for at least about 10 minutes, at least about 15 minutes, at least about 30 minutes, at least about one hour, at least about two hours, at least about three hours, at least about four hours, or at least about five hours. For instance, delayed release softgel capsules described herein may release up to about 10 wt %, up to about 9 wt %, up to about 8 wt %, up to about 7 wt %, up to about 6 wt %, up to about 5 wt %, up to about 4 wt %, up to about 3 wt %, up to about 1 wt %, or 0 wt %, of the fill material based on total weight of the fill material in acidic environment after exposure to the acidic environment for up to about 150 minutes, up to about 120 minutes, up to about 105 minutes, up to about 90 minutes, up to about 75 minutes, up to about 60 minutes, up to about 45 minutes, up to about 30 minutes, up to about 15 minutes, up to about 10 minutes, or up to about 5 minutes.

In certain embodiments, curing delayed release softgel capsules described herein (i.e., ones that are encapsulated with a pH dependent shell composition) may reduce or eliminate the number of capsules exhibiting any amount of premature release in acidic environment after about 10 minutes, about 15 minutes, about 30 minutes, about one hour, about two hours, about three hours, about four hours, or about five hours, or any sub-range within these durations. For instance, the number of cured capsules exhibiting premature release in acidic environment (after exposure to the acidic environment for up to about 5 hours, up to about 4 hours, up to about 3 hours, up to about 150 minutes, up to about 120 minutes, up to about 105 minutes, up to about 90 minutes, up to about 75 minutes, up to about 60 minutes, up to about 45 minutes, up to about 30 minutes, up to about 15 minutes, up to about 10 minutes, or up to about 5 minutes) may be up to about 30%, up to about 25%, up to about 20%, up to about 15%, up to about 10%, up to about 5%, up to about 3%, up to about 2%, up to about 1%, or 0% of the total number of capsules in the batch.

In comparison, without curing, the number of capsules (having the same composition) exhibiting premature release in acidic environment (after exposure to the acidic environment for up to about 5 hours, up to about 4 hours, up to about 3 hours, up to about 150 minutes, up to about 120 minutes, up to about 105 minutes, up to about 90 minutes, up to about 75 minutes, up to about 60 minutes, up to about 45 minutes, up to about 30 minutes, up to about 15 minutes, up to about 10 minutes, or up to about 5 minutes) may be greater than about 2%, greater than about 5%, greater than about 10%, greater than about 15%, greater than about 20%, greater than about 30%, greater than about 40%, greater than about 50%, greater than about 60%, greater than about 70%, greater than about 80%, or greater than about 90% of the total number of capsules in the batch.

In certain embodiments, curing delayed release softgel capsules described herein (i.e., ones that are encapsulated with a pH dependent shell composition) may reduce or eliminate the amount of fill material released from capsules that exhibit some premature release in acidic environment (e.g., after exposure to the acidic environment for up to about 5 hours, up to about 4 hours, up to about 3 hours, up to about 150 minutes, up to about 120 minutes, up to about 105 minutes, up to about 90 minutes, up to about 75 minutes, up to about 60 minutes, up to about 45 minutes, up to about 30 minutes, up to about 15 minutes, up to about 10 minutes, or up to about 5 minutes).

For instance, the amount of fill material released from cured capsules exhibiting some premature release in acidic environment (e.g., after exposure to the acidic environment for up to about 5 hours, up to about 4 hours, up to about 3 hours, up to about 150 minutes, up to about 120 minutes, up to about 105 minutes, up to about 90 minutes, up to about 75 minutes, up to about 60 minutes, up to about 45 minutes, up to about 30 minutes, up to about 15 minutes, up to about 10 minutes, or up to about 5 minutes) may be up to about 5 wt %, up to about 4 wt %, up to about 3 wt %, up to about 2 wt %, up to about 1 wt %, or 0% of the total weight of fill material in the capsule.

In comparison, without curing, the amount of fill material released from capsules (having the same composition) exhibiting premature release in acidic environment (e.g., after exposure to the acidic environment for up to about 5 hours, up to about 4 hours, up to about 3 hours, up to about 150 minutes, up to about 120 minutes, up to about 105 minutes, up to about 90 minutes, up to about 75 minutes, up to about 60 minutes, up to about 45 minutes, up to about 30 minutes, up to about 15 minutes, up to about 10 minutes, or up to about 5 minutes) may be greater than about 1 wt %, greater than about 2 wt %, greater than about 3 wt %, greater than about 4 wt %, greater than about 5 wt %, greater than about 6 wt %, greater than about 7 wt %, greater than about 8 wt %, greater than about 9 wt %, greater than about 10 wt %, greater than about 15 wt %, or greater than about 20 wt % of the total weight of fill material in the capsule.

In certain embodiments, the pH dependent shell composition described herein produces a robust delayed release softgel capsule that remains intact in acidic environment (e.g., stomach environment or simulated stomach environment such as simulated gastric fluid, 0.1N HCl optionally with Pepsin) for at least about 10 minutes, at least about 15 minutes, at least about 30 minutes, at least about one hour, at least about two hours, at least about three hours, at least about four hours, or at least about five hours but releases at least about 50 wt %, at least about 60 wt %, at least about 70 wt %, at least about 80 wt %, at least about 90 wt %, at least about 95 wt %, at least about 96 wt %, at least about 97 wt %, at least about 98 wt %, or at least about 98 wt % of the fill material based on total weight of the fill material in a colon environment (or simulated environments thereof such as pH 6.8 buffer medium optionally with Pancreatin) after at least about 10 minutes, after at least about 15 minutes, after at least about 20 minutes, after at least about 25 minutes, after at least about 30 minutes, after at least about 35 minutes, after at least about 40 minutes, or from any of about 10 minutes, about 15 minutes, about 20 minutes, about 25 minutes or about 30 minutes up to any of about 35 minutes, about 40 minutes, about 45 minutes, about 50 minutes, about 55 minutes, about 60 minutes, about 75 minutes, or about 90 minutes, or any single value or sub-range therein) in such colon or simulated colon environment.

In an embodiment, the pH dependent shell composition comprises: (a) gelatin, (b) dextrose, (c) a pH dependent polymer (e.g., pectin such as a low methoxyl pectin), (d) a plasticizer (e.g., glycerin, sorbitol, and combinations thereof), and optionally (e) a stabilizer and/or binder (e.g., gellan gum). The amounts and wt:wt ratios of these components may be in accordance with any of the values or ranges described hereinabove.

In an embodiment, the pH dependent shell composition consists essentially of: (a) a gelatin, (b) dextrose, (c) a pH dependent polymer (e.g., pectin such as a low methoxy pectin), (d) a plasticizer (e.g., glycerin, sorbitol, gellan gum, and combinations thereof), and optionally (e) a stabilizer and/or binder (e.g., gellan gum). The amounts and wt:wt ratios of these components may be in accordance with any of the values or ranges described hereinabove.

In an embodiment, the pH dependent shell composition consists of: (a) a gelatin, (b) dextrose, (c) a pH dependent polymer (e.g., pectin such as a low methoxyl pectin), (d) a plasticizer (e.g., glycerin, sorbitol, gellan gum, and combinations thereof), and optionally (e) a stabilizer and/or binder (e.g., gellan gum). The amounts and wt:wt ratios of these components may be in accordance with any of the values or ranges described hereinabove.

In an embodiment, the pH dependent shell composition comprises: (a) about 30 wt % to about 85 wt %, about 30 wt % to about 75 wt %, about 30 wt % to about 65 wt %, about 30 wt % to about 55 wt %, about 30 wt % to about 40 wt %, about 40 wt % to about 80 wt %, about 45 wt % to about 65 wt %, about 45 wt % to about 75 wt %, or about 50 wt % to about 70 wt % gelatin, (b) about 0.01 wt % to about 4 wt %, or from about 0.1 wt % to about 3 wt %, from about 0.2 wt % to about 2 wt %, or from about 0.01 wt % to about 0.1 wt %, or from about 0.05 wt % to about 0.5 wt %, or from about 0.1 wt % to about 0.2 wt %, or from about 0.15 wt % to about 0.25 wt %, or from about 0.2 wt % to about 0.4 wt % dextrose, (c) about 2 wt % to about 20 wt %, about 3 wt % to about 15 wt %, about 7 wt % to about 15 wt %, about 3 wt % to about 5.5 wt %, or about 7 wt % to about 12 wt % of a pH dependent polymer (e.g., pectin such as a low methoxy pectin), (d) about 15 wt % to about 45 wt %, about 15 wt % to about 40 wt %, about 20 wt % to about 35 wt %, or about 25 wt % to about 30 wt % of a plasticizer, and optionally (e) about 0.05 wt % to about 5 wt %, about 0.1 wt % to about 3 wt %, or about 0.2 wt % to about 2 wt % of stabilizer and/or binder (e.g., gellan gum). All wt % being based on the total weight of the dry pH dependent shell composition.

In an embodiment, the pH dependent shell composition consists essentially of: (a) about 30 wt % to about 85 wt %, about 30 wt % to about 75 wt %, about 30 wt % to about 65 wt %, about 30 wt % to about 55 wt %, about 30 wt % to about 40 wt %, about 40 wt % to about 80 wt %, about 45 wt % to about 65 wt %, about 45 wt % to about 75 wt %, or about 50 wt % to about 70 wt % gelatin, (b) about 0.01 wt % to about 4 wt %, or from about 0.1 wt % to about 3 wt %, or from about 0.2 wt % to about 2 wt %, or from about 0.01 wt % to about 0.1 wt %, or from about 0.05 wt % to about 0.5 wt %, or from about 0.1 wt % to about 0.2 wt %, or from about 0.15 wt % to about 0.25 wt %, or from about 0.2 wt % to about 0.4 wt % dextrose, (c) about 2 wt % to about 20 wt %, about 3 wt % to about 15 wt %, about 7 wt % to about 15 wt %, or about 3 wt % to about 5.5 wt %, or about 7 wt % to about 12 wt % of a pH dependent polymer (e.g., pectin such as a low methoxy pectin), (d) about 15 wt % to about 45 wt %, about 15 wt % to about 40 wt %, about 20 wt % to about 35 wt %, or about 25 wt % to about 30 wt % of a plasticizer, and optionally (e) about 0.05 wt % to about 5 wt %, about 0.1 wt % to about 3 wt %, or about 0.2 wt % to about 2 wt % of stabilizer and/or binder (e.g., gellan gum). All wt % being based on the total weight of the dry pH dependent shell composition.

In an embodiment, the pH dependent shell composition consists of: (a) about 30 wt % to about 85 wt %, about 30 wt % to about 75 wt %, about 30 wt % to about 65 wt %, about 30 wt % to about 55 wt %, about 30 wt % to about 40 wt %, about 40 wt % to about 80 wt %, about 45 wt % to about 65 wt %, about 45 wt % to about 75 wt %, or about 50 wt % to about 70 wt % gelatin, (b) about 0.01 wt % to about 4 wt %, or from about 0.1 wt % to about 3 wt %, or from about 0.2 wt % to about 2 wt %, or from about 0.01 wt % to about 0.1 wt %, or from about 0.05 wt % to about 0.5 wt %, or from about 0.1 wt % to about 0.2 wt % dextrose, or from about 0.15 wt % to about 0.25 wt %, or from about 0.2 wt % to about 0.4 wt % dextrose (c) about 2 wt % to about 20 wt %, about 3 wt % to about 15 wt %, about 7 wt % to about 15 wt %, or about 3 wt % to about 5.5 wt %, or about 7 wt % to about 12 wt % of a pH dependent polymer (e.g., pectin such as a low methoxy pectin), (d) about 15 wt % to about 45 wt %, about 15 wt % to about 40 wt %, about 20 wt % to about 35 wt %, or about 25 wt % to about 30 wt % of a plasticizer, and optionally (e) about 0.05 wt % to about 5 wt %, about 0.1 wt % to about 3 wt %, or about 0.2 wt % to about 2 wt % of stabilizer and/or binder (e.g., gellan gum). All wt % being based on the total weight of the dry pH dependent shell composition.

EXAMPLES

Specific embodiments of the invention will now be demonstrated by reference to the following examples. It should be understood that these examples are disclosed solely by way of illustrating the invention and should not be taken in any way to limit the scope of the present invention.

Example 1—Effect of Dextrose Concentration on Manufacturing of Composition

PH dependent shell compositions with varying concentrations of dextrose were prepared to study the effect of the dextrose concentration on the manufacturability of the composition. The pH dependent shell compositions are set forth in Table 1.

TABLE 1

| | Dry Shell Compositions | | | | |
| --- | --- | --- | --- | --- | --- |
| Ingredient | Group No. 1 wt % | Group No. 2 wt % | Group No. 3 wt % | Group No. 4 wt % | Group No. 5 wt % |
| Pectin | 8-12 | 7-11 | 7-12 | 8-13 | 6-9 |
| Gelatin | 45-65 | 38-58 | 38-58 | 38-58 | 38-58 |
| Glycerin | 28-45 | 25-35 | 25-35 | 25-35 | 25-35 |
| Water | 8-15 | 6-15 | 6-15 | 6-15 | 6-15 |
| Dextrose | 0.02-0.10 | 0.01-0.06 | 0.10-0.20 | 0.10-0.30 | None |
| Total | 100 | 100 | 100 | 100 | 100 |

The effect of varying amounts of dextrose in the pH dependent shell composition on rupture time at pH 6.8 is in Table 2.

TABLE 2

| Group No. | Dextrose (wt %) | Dissolution Results at T = 0 | | Dissolution Results at T = 6 months | |
| --- | --- | --- | --- | --- | --- |
| | | Acid Stage (0.1N HCl) | Buffer Stage (pH 6.8) | Acid Stage (0.1N HCl) | Buffer Stage (pH 6.8) |
| 1 | 0.01 | Pass (Intact for 2 hrs) | Pass (Ruptured in 8 Min) | Pass (Intact for 2 hrs) | Ruptured in 25 minutes |
| 2 | 0.05 | Pass (Intact for 2 hrs) | Pass (Ruptured in 4 Min) | Pass (Intact for 2 hrs) | No rupture for 60 minutes |
| 3 | 0.1 | Pass (Intact for 2 hrs) | Pass (Ruptured in 3 Min) | Pass (Intact for 2 hrs) | No rupture for 60 minutes |
| 4 | 0.15 | Pass (Intact for 2 hrs) | Pass (Raptured in 11 Min) | Pass (Intact for 2 hrs) | No rupture for 60 minutes |
| 5 | None | Failed (Ruptured in 90 minutes) | N/A | Pass (Intact for 2 hrs) | Ruptured in 28 minutes |

Dextrose is a reducing sugar and is believed to interact with gelatin by causing the gelatin to cross-link. When gelatin is crosslinked, its solubility is reduced. It was shown that dextrose stabilizes (i.e., reduces leakage) the pectin softgel capsule in acidic medium. Dextrose can also contribute to the amount of active agent (vitamins, minerals, supplements, or pharmaceutical ingredients) released at the buffer medium as well as to the dissolution time of the active agent in buffer medium. This is illustrated with respect to samples 3 and 4 from Table 2 in Example 7 below.

Although Table 2 shows that some capsules (e.g., groups 2, 3, and 4) did not rupture in pH 6.8 phosphate buffer for 60 minutes, upon addition of pancreatin to the buffer medium (which is believed to better mimic in-vivo conditions), the shell composition dissolved in less than 45 minutes as shown in Example 7 below.

Example 2—Effect of Curing on Capsule Release Properties pH dependent shell compositions were prepared to study the effect of curing on the release properties of the capsules. The pH dependent shell compositions are set forth in Table 3.

TABLE 3

| Gel Mass Formulations in wt % in Dry Capsule Shell | | | |
| --- | --- | --- | --- |
| Ingredient | Lot 1 | Lot 2 | Lot 3 |
| Non-amidated pectin | 7.0-12.0 | 8.0-12.0 | 8.0-12.0 |
| Dextrose | 0.02-0.10 | 0.10-1.0 | 0.10-1.0 |
| Glycerin | 28-45 | 28-45 | 28-45 |
| Gelatin | 45-65 | 45-65 | 45-65 |
| Water | 8-15 | 8-15 | 8-15 |
| Total | 100 | 100 | 100 |
| Additional Properties | | | |
| Weight non-amidated pectin to weight gelatin ratio | 1:7 | 1:7.5 | 1:7.5 |
| Weight glycerin to weight gelatin ratio | 1:2 | 1:2 | 1:2 |
| Gel mass viscosity (cPs) | 115,000 | 121,000 | 121,000 |
| % Capsules having Premature Release Prior to Curing | 67% | 42% | 50% |

Existing commercial products exhibit premature release in a large number of capsules, increased amounts of fill material prematurely released, and in some instances almost a 100 wt % of the fill material being released in acidic medium within a 10 minute duration.

Coated softgel capsules were contemplated but those did not dissolve in buffer medium for an extended duration (longer than about 60 minutes and in some instances as long as 120 minutes). The long dissolution in buffer medium was believed to suggest that coated softgel capsules would not be bioavailable. This along with the challenge of two step manufacturing process encouraged exploration of pH dependent shell compositions to form a delayed release softgel capsule without a separate coating.

The pH dependent shell compositions set forth in Table 3 were used to form pectin softgels which reduced the occurrence of premature release and the amount of fill material that is prematurely released to a certain extent (as compared to existing commercial products).

However, prior to curing, a significant fraction of the softgel capsules in each lot still continued to exhibit some premature release of the fill material in acidic environment (e.g., 0.1N HCl), as summarized in Table 3 in the "% capsules having premature release prior to curing." About 60 to about 72 capsules were tested from each lot to assess the % capsules having premature release prior to curing.

In certain embodiments, about 10 wt % of the fill material was released from capsules having premature release, prior to curing. In certain embodiments, more than 10 wt % of the fill material or less than 10 wt % of the fill material was released from capsules having premature release, prior to curing.

As will be shown in subsequent examples, curing reduced the occurrence of premature release, the amount of fill material released upon occurrence of premature release, and in some instances eliminated premature release altogether.

The pectin softgel capsules were cured to enhance their stability in acidic environment (e.g., 0.1N HCl). The pectin softgels were packaged in cartons (for bulk) or in high density polyethylene (HDPE) bottles and placed into an oven heated to 40° C. No humidity controls were used. The only variable across samples was the curing time. The curing study results of lots 1, 2, and 3 are summarized in Table 4 below.

TABLE 4

| Results of Curing Studies | | | | | |
| --- | --- | --- | --- | --- | --- |
| | | | | Dissolution After Curing | |
| Sample | Prior to Curing % Capsules having Premature Release | No. of Capsules Tested | Curing Time | 0.1N HCl No. Capsules having Premature Release (% of total capsules) | pH 6.8 buffer (Rupture Time) |
| Lot 1 | 67% | 12 | 24 hours | 3 (25%) | 8 minutes |
| | | 36 | 48 hours | None | 7 minutes |
| Lot 2 | 42% | 60 | 48 hours | 1 (1.7%) | 7 minutes |
| | | 72 | 72 hours | None | 9 minutes |
| Lot 3 | 50% | 60 | 48 hours | None | 7 minutes |
| | | 60 | 72 hours | None | 7 minutes |

The dissolution after curing was assessed in accordance with the USP enteric testing method for a two stage enteric dissolution test applicable to uncoated enteric softgels. Unless specified otherwise, the acidic medium, buffer medium, apparatus, and dissolution test conditions for all dissolution testing throughout this description was performed in accordance with this two stage enteric dissolution test.

A USP Apparatus II with paddles was used, at a paddle speed of 50 rpm at 37° C. The acidic stage medium was 0.1N HCl. The buffer stage medium was pH 6.8 phosphate buffer. For vitamin mineral supplements and/or nutraceutical products, enteric capsules should remain intact for at least 60 minutes in acidic medium to pass the first stage and rupture within 45 minutes in buffer stage medium to pass the second stage. For pharmaceutical products, enteric capsules should remain intact for at least 120 minutes in acidic medium to pass the first stage and rupture within 45 minutes in buffer stage medium to pass the second stage.

Curing of the softgel capsules was assessed at 24 hours, 48 hours, 72 hours, 120 hours, 168 hours, and 288 hours. Although only data up to 72 hours is presented herein.

Table 5 depicts the amount of premature release of fill material from pectin softgel capsules of lot 3, prior to curing and after curing, in acidic medium following a USP enteric test criteria at the end of 2 hours. The maximum amount of fill material that was released was 5%. The pectin softgel capsules in lot 3 included fish oil (which includes docosahexaenoic acid (DHA) and eicosapentaenoic acid (EPA)) in the fill material.

TABLE 5

Lot 3—Amount of Fill Material Prematurely Released in Acidic
Media (0.1N HCl) Following USP Enteric Test Criteria

| Vessel | Dissolution in 0.1N HCl after 2 hours, Prior to Curing | | Dissolution in 0.1N HCl after 2 hours, After Curing for 72 hours | |
| --- | --- | --- | --- | --- |
| No. | % EPA | % DHA | % EPA | % DHA |
| V1 | 5 | 4 | 0 | 0 |
| V2 | 3 | 3 | 0 | 0 |
| V3 | 3 | 3 | 0 | 0 |
| V4 | 3 | 3 | 0 | 0 |
| V5 | 1 | 1 | 0 | 0 |
| V6 | 3 | 3 | 0 | 0 |

The curing data showed that curing significantly reduced or eliminated premature release of fill material from pectin capsules in acidic medium resulting in capsules with robust enteric properties and high quality enteric product.

Note that all of the pectin softgel capsules tested in Table 5 dissolved in pH 6.8 buffer within 15 minutes.

Example 3—Enteric Dissolution Data in Simulated Gastric Fluid (SGF) with Pepsin Cured pectin capsules, having the gel mass formulas summarized in Table 6A, were subjected to an enteric rupture testing using SGF (0.1N HCl) with pepsin (to simulate in-vivo conditions in humans) for two stage enteric dissolution studies.

TABLE 6A

Gel Mass Formulations in wt % in Dry Capsule Shell

| Ingredient | Lot 4 | Lot 5 |
| --- | --- | --- |
| Non-amidated pectin | 7.0-11.0 | 8.0-13.0 |
| Dextrose | 0.02-0.08 | 0.02-0.08 |
| Glycerin | 18-42 | 18-42 |
| Gelatin | 45-65 | 45-65 |
| Water | 8-15 | 8-15 |
| Total | 100 | 100 |

TABLE 6B

Dissolution of Pectin Softgel Capsules from Table
6A in Acidic Medium with and without Pepsin

| Lot No | 0.1N HCl | 0.1N HCl with Pepsin |
| --- | --- | --- |
| Lot 4 | Intact for 120 minutes | Intact for 120 minutes |
| Lot 5 | Intact for 120 minutes | Intact for 120 minutes |

Pepsin did not affect the dissolution of pectin shells in 0.1N HCl medium when an appropriate shell composition, e.g., Gelatin to Pectin ratio is used. In lots 4 and 5, illustrated in Tables 6A and 6B, the gelatin to pectin w:w ratio was 7:1. Without being construed as limiting, it is believed that the pectin softgels are robust and that the gelatin-pectin networks are strong enough to withstand the effect of pepsin as evidenced by the pectin softgel capsules remaining intact for 120 minutes in 0.1N HCl even in the presence of pepsin which represents a Biorelevant media unlike the Pharmacopeial method which does not include an enzyme. Hence, it is believed that the pectin softgel capsules will also be sufficiently robust in-vivo.

Example 4—Modulation of Pectin Capsule Rupture Time in Enteric Media by Changing the Gelatin to Pectin Ratio Pectin softgel capsules were prepared with varying Gelatin to Pectin ratio. The composition of the various lots is summarized in Table 7B below. The rupture time of the pectin capsules in SGF (0.1N HCl) with pepsin varied with varying Gelatin to Pectin ratio, as summarized in Table 7A below.

TABLE 7A

| Lot No | Gelatin-Pectin ratio | 0.1N HCl with Pepsin |
| --- | --- | --- |
| Lot 6 | 18:1 | Ruptured at 12 minutes |
| Lot 7 | 12:1 | Ruptured at 36 minutes |
| Lot 8 | 8:1 | Intact for 120 minutes |
| Lot 1 | 7:1 | Intact for 120 minutes |

TABLE 7B

Gel Mass Formulas Based on Dry Shell Composition
for Gelatin-Pectin Ratio Study (wt %)

| Ingredient | Lot 6 | Lot 7 | Lot 8 | Lot 1 |
| --- | --- | --- | --- | --- |
| Pectin | Non-amidated pectin 3.0-8.0 | Amidated pectin 6.0-10.0 | Non-amidated pectin 8.0-15.0 | Non-amidated pectin 7.0-12.0 |
| Dextrose | 0 | 0 | 0.02-0.10 | 0.02-0.10 |
| Glycerin | 8-15 | 21-41 | 8-15 | 28-45 |
| Sorbitol | 21-32 | 0 | 21-32 | 0 |
| Gelatin | 44-65 | 42-61 | 44-65 | 45-65 |
| Water | 8-15 | 8-15 | 8-15 | 8-15 |
| Total | 100.0 | 100.0 | 100.0 | 100.0 |

All of the pectin softgel capsules from Table 7A ruptured in pH 6.8 buffer within 45 minutes. Table 7A illustrates that the rupture time of the pectin softgel capsules in acidic medium may be modulated by changing the gelatin to pectin ratio.

Example 5—Effect of Softgel Ribbon Thickness on the Enteric Performance of the Pectin Softgel Capsule Pectin softgel capsules were prepared with varying ribbon thicknesses. The compositions of the dry pH dependent shell composition for lots manufactured with varying ribbon thicknesses are summarized in Table 8A below. The dissolution of the pectin capsules of varying ribbon thickness, after curing for about 72 to 96 hours, in SGF (0.1N HCl) and in pH 6.8 buffer was evaluated. The results are summarized in Table 8B below.

TABLE 8A

| Gel Mass Formulas Based on Dry Shell Composition for Ribbon Thickness Study (wt %) | | | | | |
|---|---|---|---|---|---|
| Ingredient | Lot 9 | Lot 10 | Lot 11 | Lot 12 | Lot 13 | Lot 14 |
| Pectin | Amidated pectin 6.5-10.0 | Non-amidated pectin 8.0-12.0 | Amidated pectin 6.5-10.0 | Non-amidated pectin 7.0-11.0 | Non-amidated pectin 8.0-12.0 | Non-amidated pectin 8.0-13.0 |
| Dextrose | None | 0.020-0.15 | None | 0.02-0.06 | 0.020-0.15 | 0.02-0.10 |
| Glycerin | 22-40 | 21-41 | 22-40 | 18-42 | 21-41 | 18-42 |
| Gelatin | 42-58 | 44-61 | 42-58 | 45-65 | 44-61 | 45-65 |
| Water | 8-15 | 8-15 | 8-15 | 8-15 | 8-15 | 8-15 |
| Total | 100.0 | 100.0 | 100.0 | 100.0 | 100.0 | 100.0 |

TABLE 8B

Dissolution of Cured Softgel Pectin Capsules with Varying Ribbon Thickness

| | | Dissolution on Cured Pectin Softgel Capsules | |
|---|---|---|---|
| Lot No | Ribbon Thickness (inches) | 0.1N HCl (120 minutes) | pH 6.8 Buffer (Rupture Time, min) |
| Lot 9 | 0.028 | Intact | 7 |
| Lot 10 | 0.030 | Intact | 1 |
| Lot 11 | 0.032 | Intact | 8 |
| Lot 12 | 0.034 | Intact | 5 |
| Lot 13 | 0.036 | Intact | 3 |
| Lot 14 | 0.038 | Intact | 7 |

TABLE 9

Viscosity of Aged pH Dependent Shell Compositions Aged

| | Aging Time (hours) | Viscosity (cPs) | % Viscosity Reduction from aging time of 0 hours |
|---|---|---|---|
| Non-amidated pectin | 0 | 140,000 | N/A |
| | 24 hours at 60° C. | 90,000 | About 36% |
| | 48 hours at 60° C. | 90,000 | About 36% |
| | 72 hours at 60° C. | 75,000 | About 46% |
| | 96 hours at 60° C. | 75,000 | About 46% |
| Amidated Pectin | 0 | 105,000 | N/A |
| | 24 hours at 60° C. | 70,000 | About 33% |
| | 48 hours at 60° C. | 55,000 | About 48% |
| | 72 hours at 60° C. | 35,000 | About 67% |
| | 96 hours at 60° C. | 40,000 | About 62% |

The dissolution results depicted in Table 8B illustrate that pectin softgel capsules, having a ribbon thickness ranging from 0.028 inches to 0.038 inches, after curing, were shown to be robust and were shown to meet the enteric criteria for pharmaceutical products and for VMS (vitamin, mineral, supplements) products. This thickness range should not be construed as limiting. In certain embodiments, thicker ribbons or thinner ribbons may also be utilized.

Example 6—pH Dependent Shell Composition Viscosity Upon Aging

Pectin and gelatin interact with each other to form networks which contribute to significant increases in gel mass viscosity shown in FIG. 1. The interaction between pectin and gelatin is believed to contribute to the capsule shell composition's delayed release properties. However, as seen in FIG. 1, the viscosity of gel mass of the pH dependent shell composition decreases over time. The viscosities and % reduction are summarized in Table 9 below.

The viscosity in this example and throughout the description was measured using a rheometer (HAAKE Rheostress 6000 by Thermo Fisher) at 60° C. The tests were performed at ambient conditions. The gel mass samples were loaded onto the platform of the rheometer, which was maintained at 60° C. A 40 mm disc oscillated at a frequency of 0.1 Hz to provide a fixed shear rate. The viscosity was obtained by measuring the shear stress and shear rate.

As can be seen from Table 9, the viscosity of non-amidated pectin decreases by a smaller percentage as compared to the viscosity of amidated pectin, after 48 hours of aging at 60° C., 72 hours of aging at 60° C., and 96 hours of aging at 60° C.

The decrease in viscosity is believed to be caused by the thermal degradation of the molecular chain lengths of pectin and gelatin. Despite this viscosity reduction, the gel masses of the pH dependent shell compositions maintain the a viscosity suitable for manufacturability and machinability even after holding the composition in heat at 60° C. for 4 days. Furthermore, softgel capsules manufactured with the aged gel still have satisfactory pH dependent delayed release properties.

Example 7—Effect of Dextrose Addition on Dissolution Time in Buffer Medium in the Presence of Pancreatin The dissolution of pectin softgel capsules with varying dextrose amount in the pH dependent shell composition was evaluated in acid medium (0.1N HCl, pH=1.2) and in buffer medium (pH 6.8 phosphate buffer with 1% pancreatin). The dissolution of these pectin softgel capsules was evaluated in accordance with the two step enteric dissolution test described in Example 2 above. The results are summarized in Table 10 below.

TABLE 10

| Group | Dextrose % | | 2-Stage Dissolution Test | | | | | | |
|---|---|---|---|---|---|---|---|---|---|
| | | | V1 | V2 | V3 | V4 | V5 | V6 | Avg |
| F3 (40° C./ 75% RH) | 0.10% | Acid Stage (pH = 1.2) | Intact | Intact | Intact | N/A | N/A | N/A | Intact |
| | | Buffer Stage (pH = 6.8) w/ 1% Pancreatin | 25 mins | 23 mins | 29 mins | N/A | N/A | N/A | 25.7 mins |
| F4 (40° C./ 75% RH) | 0.15% | Acid Stage (pH = 1.2) | N/A | N/A | N/A | Intact | Intact | Intact | Intact |
| | | Buffer Stage (pH = 6.8) w/ 1% Pancreatin | N/A | N/A | N/A | 43 mins | 39 mins | 35 mins | 39.0 mins |

Three samples from each of groups 3 and 4 from Tables 1 and 2 above (Example 1) were evaluated and the average was summarized. As seen in Table 10, samples from group 3 (0.1 wt % dextrose in the pH dependent shell composition), remained intact for 120 minutes in acidic medium (0.1N HCl, pH 1.2) and ruptured in buffer medium (pH 6.8 phosphate buffer with 1% Pancreatin) in about 25.7 minutes (on average). Samples from group 4 (0.15 wt % dextrose in the pH dependent shell composition), remained intact for 120 minutes in acidic medium (0.1N HCl, pH 1.2) and ruptured in buffer medium (pH 6.8 phosphate buffer with 1% Pancreatin) in about 39.0 minutes (on average).

Hence, as shown in Table 10, the amount of dextrose in the pH dependent shell composition can be tuned to attain a target dissolution/disintegration/rupture time in buffer medium with pancreatin. This is useful for targeting colonic delivery of active agents, such as, vitamins, minerals, supplements, or pharmaceutical ingredients.

Example 8—Chemical Stability of the Pectin Softgel Capsule

Table 11 below depicts the chemical stability of fish oil encapsulated in a pectin pH dependent shell composition, according to embodiments described herein, after storage for 6 months at ambient conditions and at 40° C. and 75% relative humidity (RH). Acceptable capsules should have EPA TG≥160 mg/g, DHA TG≥100 mg/g, peroxide≤5 meq $O_2$/kg, p-Anisidine≤20, a dissolution time of more than 120 minutes in 0.1N HCl (pH 1.2), and a dissolution time of up to 45 minutes in buffer medium (pH 6.8 phosphate buffer). The values for these parameters are summarized in Table 11 for the control (fish oil raw material), the delayed release softgel pectin capsule stored at ambient conditions for 6 months, and the delayed release pectin softgel capsule stored at 40° C. and 75% RH for 6 months.

TABLE 11

| | | | | | Dissolution | |
|---|---|---|---|---|---|---|
| Sample 19PP-59Lot 10 | EPATG (≥160 mg/g) | DHATG (≥100 mg/g) | Peroxide (≤5 meq $O_2$/kg) | p-Anisidine (≤20) | 0.1N HCl pH 1.2 | pH 6.8 Phosphate Buffer |
| Fish Oil Raw Material | 172 | 124 | 0.9 | 11.0 | N/A | N/A |
| At 1 = 6 months Ambient | 174 | 123 | 2.4 | 12.9 | Pass (Intact for 120 minutes) | 15 minutes |
| At 1 = 6 months 40° C./75% RH | 174 | 123 | 2.5 | 14.8 | Pass (Intact for 120 minutes) | 25 minutes |

The accelerated stability data (summarized in Table 11) demonstrates that the pH resistant pectin shell composition, according to embodiments, protected the fill material (e.g., fish oil constituents) from oxidation, as evident from the insignificant/substantial similarity in the peroxide and p-Anisidine values and EPA and DHA assays after 6 months (at ambient conditions as well as at stressed conditions of 40° C. and 75% RH) as compared to the raw material.

Example 9—Valproic Acid Pectin Softgel Capsule

Table 12A below depicts the stability of the dissolution profile of valproic acid encapsulated in a pectin pH dependent shell composition (the gel formula of the dry shell composition is summarized in Table 12B), according to embodiments described herein, at T=0, after storage for 3 months (T=3 months) at 40° C. and 75% relative humidity (RH), and after storage for 6 months (T=6 months) and at 40° C. and 75% RH. As evidenced in Table 12A, the dissolution profile of the pH dependent shell composition, after storage for 3 months at 40° C. and 75% RH and after storage for 6 months at 40° C. and 75% RH, remains substantially similar to the dissolution profile at T=0.

TABLE 12A

| Dissolution of Valproic Acid Encapsulated In A Pectin pH Dependent Shell Composition | | | | | | |
|---|---|---|---|---|---|---|
| | | T = 0 | | T = 3 Months 40° C./75% RH | | T = 6 Months 40° C./75% RH |
| Lot No. | Fill Material | Acid Stage (0.1N HCl, pH 1.2) | Buffer Stage (pH 6.8 phosphate buffer) | Acid Stage (0.1N HCl, pH 1.2) | Buffer Stage (pH 6.8 phosphate buffer) | Acid Stage (0.1N HCl, pH 1.2) | Buffer Stage (pH 6.8 phosphate buffer) |
| Lot 15 | Valproic Acid | Intact (120 minutes) | Pass (9 min) | Intact (120 minutes) | Pass (12 min) | Intact (120 minutes) | Pass (11 min) |

TABLE 12B

| Gel Mass Formulations in wt % in Dry Capsule Shell | |
|---|---|
| Ingredient | Lot 15 |
| Amidated pectin | 6.5-8.0 |
| Dextrose | None |
| Glycerin | 20-45 |
| Gelatin | 42-56 |
| Water | 8-15 |
| Total | 100 |

Example 10—Physical Attributes of Pectin Softgel Capsule

Delayed release softgel capsules having the pH dependent shell composition described herein are robust as evidenced based on the physical attributes summarized in Table 13 below.

TABLE 13

| Physical Attributes of Delayed Release Softgel Capsules | |
|---|---|
| Parameters | Typical Specifications |
| Shell Moisture (%) | 6-15 |
| Hardness (Newtons) | 7-14 |
| Equilibrium Relative Humidity (%) | 30-45 |
| Burst Strength (kg) | 60-120 |

The shell moisture was determined by loss on drying method. A pH dependent capsule shell composition sample of 1 to 2 grams were placed into a 105° C. oven for 17 hours. The initial weight of the sample was recorded. After drying the sample in the oven at 105° C. for 17 hours, the final weight of the sample was recorded. The percentage of weight loss, calculated in accordance with the below equation, was defined as the shell moisture:

$$\% \text{ Weight Lost} = \frac{(\text{Initial Weight}) - (\text{Final Weight})}{(\text{Initial Weight})} \cdot 100\%$$

The capsule hardness was determined using a hardness tester. The force required to cause a 2.0 mm deformation of the capsule in Newton was defined as the capsule hardness.

Equilibrium Relative Humidity (%) was defined as the humidity condition at which the capsule maintained a constant total weight. It was determined using environmental chambers maintained at constant humidity using saturated salt solutions.

Burst strength was determined using a texture analyzer. The texture analyzer compressed the capsule until the capsule burst. The force, in kilograms, required to make the capsule burst was defined as burst strength.

Example 11—Exemplary Composition of a Pectin and Gellan Gum Delayed Release Softgel Capsule Delayed release softgel capsule that includes a combination of pectin and gellan gum was prepared. The formulation based on dry shell composition is summarized in Table 14 below.

TABLE 14

Gel Mass Formulations in wt % in Dry Capsule Shell

| Ingredient | Lot 15 |
|---|---|
| Pectin | 7.0-10.5 |
| Dextrose | 0.02-0.5 |
| Glycerin | 15-25 |
| Gelatin | 35-50 |
| Sorbitol Solution | 25-32 |
| Gellan Gum | 0.1-2.0 |
| Water | 6-15 |
| Total | 100 |

Example 12—Stability Studies of Gel Mass Compositions According to Embodiments Described Herein The stability of gel mass compositions according to embodiments described herein was evaluated. Three gel masses containing various levels of dextrose were prepared. From the gel masses, softgel capsules were prepared containing 1000 mg of fish oil. The softgel capsules were dried and packaged into HDPE bottles then sealed by induction. The formula of each gel mass (based on the dry shell mass) is set forth in Table 15. As shown in Table 15, the base gel formula was identical with the amounts of dextrose changed to 0.05 wt %, 0.10 wt % and 0.15 wt %.

TABLE 15

Gel mass compositions evaluated for stability

| Item Description | 19MC-03 wt % | 19MC-02 wt % | 19MC-05 wt % |
|---|---|---|---|
| Gelatin | 59.4 | 59.4 | 59.4 |
| Glycerin | 32.3 | 32.3 | 32.3 |
| Pectin | 8.3 | 8.3 | 8.3 |
| Dextrose | 0.05 | 0.10 | 0.15 |
| Total | 100.05 | 100.10 | 100.15 |

All three batches of the softgel capsules packaged in HDPE bottles were placed into 40° C./75% Relative Humidity stability chambers. Samples were taken out at 3 and 6 month time points and tested. During the stability testing, the enzyme was added before the beginning of the buffer stages. The stability and testing results are summarized in Tables 16A-16D. The results show that the formulations containing dextrose in amounts of about 0.05 wt % to about 0.10 wt % maintain stability at accelerated conditions at about 6 months. When pancreatin was included, the formulations containing 0.15 wt % showed good stability at 6 months at accelerated conditions.

TABLE 16A

Stability of softgel capsule formulations described in Table 15 at 0 and 1 month

| | | T = 0 | | T = 1 Months 40° C./75% RH | |
|---|---|---|---|---|---|
| Lot No. | Dextrose wt % | Acid Stage (0.1N HCl) | Buffer Stage (pH 6.8) | Acid Stage (0.1N HCl) | Buffer Stage (pH 6.8) |
| 19MC-03 | 0.05 | Pass (Intact for 2 hrs) | Pass (Ruptured in 4 Min) | Pass (Intact for 2 hrs) | Pass (Ruptured in 10 Min) |
| 19MC-02 | 0.10 | Pass (Intact for 2 hrs) | Pass (Ruptured in 3 Min) | Pass (Intact for 2 hrs) | Pass (Ruptured in 4 Min) |
| 19MC-05 | 0.15 | Pass (Intact for 2 hrs) | Pass (Ruptured in 11 Min) | Pass (Intact for 2 hrs) | Pass (Ruptured in 15 Min) |

TABLE 16B

Stability of softgel capsule formulations described in Table 15 at 0 and 3 months

| | | T = 0 | | T = 3 Months 40° C./75% RH | |
|---|---|---|---|---|---|
| Lot No. | Dextrose wt % | Acid Stage (0.1N HCl) | Buffer Stage (pH 6.8) | Acid Stage (0.1N HCl) | Buffer Stage (pH 6.8) |
| 19MC-03 | 0.05 | Pass (Intact for 2 hrs) | Pass (Ruptured in 4 Min) | Pass (Intact for 2 hrs) | Pass (Ruptured in 24 Min) |
| 19MC-02 | 0.10 | Pass (Intact for 2 hrs) | Pass (Ruptured in 3 Min) | Pass (Intact for 2 hrs) | Pass (Ruptured in 12 Min) |
| 19MC-05 | 0.15 | Pass (Intact for 2 hrs) | Pass (Ruptured in 11 Min) | Pass (Intact for 2 hrs) | Fail (Not ruptured in 60 Min) |

TABLE 16C

Stability of softgel capsule formulations described in Table 15 at 0 and 6 months

| | | T = 0 | | T = 6 Months 40° C./75% RH | |
|---|---|---|---|---|---|
| Lot No. | Dextrose wt % | Acid Stage (0.1N HCl) | Buffer Stage (pH 6.8) | Acid Stage (0.1N HCl) | Buffer Stage (pH 6.8) |
| 19MC-03 | 0.05 | Pass (Intact for 2 hrs) | Pass (Ruptured in 4 Min) | Pass (Intact for 2 hrs) | Fail (Not Rupture in 60 mins) |
| 19MC-02 | 0.10 | Pass (Intact for 2 hrs) | Pass (Ruptured in 3 Min) | Pass (Intact for 2 hrs) | Fail (Not Rupture in 60 mins) |
| 19MC-05 | 0.15 | Pass (Intact for 2 hrs) | Pass (Ruptured in 11 Min) | Pass (Intact for 2 hrs) | Fail (Not ruptured in 60 Min) |

TABLE 16D

| Lot No. | Dextrose wt % | T = 0 | | T = 6 Months 40° C./75% RH | | |
|---|---|---|---|---|---|---|
| | | Acid Stage (0.1N HCl) | Buffer Stage (pH 6.8) | Acid Stage (0.1N HCl) | Buffer Stage (1% Pancreatin pH 6.8) | Buffer Stage (1% Pancreatin pH 8.5) |
| 19MC-03 | 0.05 | Pass (Intact for 2 hrs) | Pass (Ruptured in 4 Min) | Pass (Intact for 2 hrs) | Pass (Ruptured in 26 Min) | N/A |
| 19MC-02 | 0.10 | Pass (Intact for 2 hrs) | Pass (Ruptured in 3 Min) | N/A | N/A | N/A |
| 19MC-05 | 0.15 | Pass (Intact for 2 hrs) | Pass (Ruptured in 11 Min) | Pass (Intact for 2 hrs) | Pass (Ruptured in 39 Min) | Pass (Ruptured in 22 Min) |

Table 17 summarizes the stability results for softgel capsules stored at ambient condition for two years.

TABLE 17

Stability results for softgel capsules at ambient condition

| Batch No. | T = 24 Months Ambient Condition | | |
|---|---|---|---|
| | Acid Stage (0.1N HCl) | Buffer Stage (1% Pancreatin pH 6.8) | Buffer Stage (1% Pancreatin pH 8.5) |
| 19MC-03 | Pass (Intact for 2 hrs) | Pass (Ruptured in 18 Min) | Pass (Ruptured in 11 Min) |
| 19MC-05 | Pass (Intact for 2 hrs) | Pass (Ruptured in 23 Min) | Pass (Ruptured in 13 Min) |

As shown in Table 17, formulations containing about 0.05 wt % to about 0.1 wt % had good stability at room temperature conditions for two years. In summary, the addition of various amounts of dextrose improved the robustness of the enteric property of the pectin softgel capsules, which provided possibility to achieve colonic delivery of certain drug molecules.

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

The present invention has been described with reference to specific exemplary embodiments thereof. The specification and drawings are, accordingly, to be regarded in an illustrative rather than a restrictive sense. Various modifications of the invention in addition to those shown and described herein will become apparent to those skilled in the art and are intended to fall within the scope of the appended claims.

What is claimed is:

1. A delayed release softgel capsule comprising:
   (a) a fill material; and
   (b) a shell derived from a pH dependent shell composition,
   wherein the fill material comprises at least one pharmaceutically active ingredient,
   wherein the pH dependent shell composition comprises gelatin, pectin, and dextrose,
   wherein the shell ruptures in the colon environment, and
   wherein the pH dependent shell composition has a viscosity ranging from about 60,000 cPs to about 150,000 cPs when measured using a rheometer at 60° C. at ambient conditions.

2. The delayed release softgel capsule of claim 1, wherein the pH dependent shell composition further comprises a plasticizer.

3. The delayed release softgel capsule of claim 1, wherein the pectin is low methoxyl pectin.

4. The delayed release softgel capsule of claim 1, wherein the pectin is selected from the group consisting of amidated pectin, non-amidated pectin and combinations thereof.

5. The delayed release softgel capsule of claim 1, wherein the pH dependent shell composition comprises about 40 wt % to about 80 wt % of a gelatin, based on the dry pH dependent shell composition weight.

6. The delayed release softgel capsule of claim 1, wherein the pH dependent shell composition comprises about 2 wt % to about 20 wt % of pectin, based on the dry pH dependent shell composition weight.

7. The delayed release softgel capsule of claim 1, wherein the pH dependent shell composition comprises about 0.01 wt % to about 4 wt % of dextrose, based on the dry pH dependent shell composition weight.

8. The delayed release softgel capsule of claim 2, wherein the plasticizer is selected from the group consisting of glycerin, sorbitol and combinations thereof.

9. The delayed release softgel capsule of claim 1, wherein the capsule dissolves/disintegrates after at least about 10 minutes, after at least about 15 minutes, after at least about 20 minutes, after at least about 25 minutes, after at least about 30 minutes, after at least about 35 minutes, after at least about 40 minutes, or from any of about 10 minutes, about 15 minutes, about 20 minutes, about 25 minutes or about 30 minutes up to any of about 35 minutes, about 40 minutes, about 45 minutes, about 50 minutes, about 55 minutes, about 60 minutes, about 75 minutes, or about 90 minutes in an intestinal environment based on a dissolution/disintegration test performed in a USP Apparatus II with paddles at a speed of 50 rpm in pH 6.8 phosphate buffer, optionally with pancreatin.

10. The delayed release softgel capsule of claim 1, wherein the capsule dissolves/disintegrates in at least about 15 minutes, at least about 30 minutes, at least about one hour, at least about two hours, at least about three hours, at least about four hours, or at least about five hours in an acidic medium based on a dissolution/disintegration test performed in a USP Apparatus II with paddles at a speed of 50 rpm in 0.1N HCl, optionally with pepsin.

11. The delayed release softgel capsule of claim 1 that is free of additional pH dependent polymers.

12. The delayed release softgel capsule of claim 1, wherein the pH dependent shell composition has a gelatin to pectin w:w ratio ranging from about 2:1 to about 20:1 or from about 6:1 to about 18:1.

13. The delayed release softgel capsule of claim 1, wherein the pH dependent shell composition has a plasticizer to gelatin w:w ratio ranging from about 5:1 to about 1:5.

14. A method for tuning the pH dependent dissolution profile of the delayed release softgel capsule of claim 1, the method comprising adjusting an amount of pectin and dextrose in the pH dependent shell composition to attain a target pH dependent dissolution profile in acidic medium and/or in buffer medium.

15. A method of treating a condition comprising, administering to a subject in need thereof the delayed release softgel capsule according to claim 1.

16. A method of reducing incidence of belching comprising, administering to a subject in need thereof the delayed release softgel capsule of claim 1.

17. A delayed release softgel capsule comprising:
(a) a fill material; and
(b) a shell derived from a pH dependent shell composition,
wherein the fill material comprises at least one pharmaceutically active ingredient,
wherein the pH dependent shell composition comprises gelatin, a pH dependent polymer, and dextrose,
wherein the pH dependent shell composition ruptures in the colon environment, and
wherein the pH dependent shell composition has a viscosity ranging from about 60,000 cPs to about 150,000 cPs when measured using a rheometer at 60° C. at ambient conditions.

18. A method of delivering a drug to the colon of a patient comprising orally administering the delayed release softgel capsule of claim 1.

* * * * *